United States Patent
Gaublomme et al.

(10) Patent No.: US 11,072,816 B2
(45) Date of Patent: Jul. 27, 2021

(54) SINGLE-CELL PROTEOMIC ASSAY USING APTAMERS

(71) Applicants: THE BROAD INSTITUTE, INC., Cambridge, MA (US); MASSACHUSETTS INSTITUTE OF TECHNOLOGY, Cambridge, MA (US)

(72) Inventors: Jellert Gaublomme, Cambridge, MA (US); Aviv Regev, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 98 days.

(21) Appl. No.: 15/970,791

(22) Filed: May 3, 2018

(65) Prior Publication Data

US 2018/0320224 A1  Nov. 8, 2018

Related U.S. Application Data

(60) Provisional application No. 62/500,784, filed on May 3, 2017.

(51) Int. Cl.
| | | |
|---|---|---|
| *C12Q 1/6818* | (2018.01) | |
| *G01N 33/68* | (2006.01) | |
| *C12N 15/115* | (2010.01) | |
| *G01N 33/543* | (2006.01) | |

(52) U.S. Cl.
CPC .......... *C12Q 1/6818* (2013.01); *C12N 15/115* (2013.01); *G01N 33/54366* (2013.01); *G01N 33/6803* (2013.01); *G01N 33/6818* (2013.01); *C12N 2310/16* (2013.01); *G01N 2458/10* (2013.01)

(58) Field of Classification Search
CPC .............. C12Q 1/6818; G01N 33/6818; C12N 15/115; C12N 2310/16
See application file for complete search history.

(56) References Cited

U.S. PATENT DOCUMENTS

| | | | |
|---|---|---|---|
| 4,683,202 A | 7/1987 | Mullis et al. | |
| 4,683,195 A | 11/1990 | Mullis et al. | |
| 5,580,737 A | 12/1996 | Polisky et al. | |
| 5,660,985 A | 8/1997 | Pieken et al. | |
| 6,033,880 A | 3/2000 | Haff et al. | |
| 6,524,456 B1 | 2/2003 | Ramsey et al. | |
| 6,617,145 B2 | 9/2003 | Boone et al. | |
| 7,041,481 B2 | 5/2006 | Anderson et al. | |
| 7,129,091 B2 | 10/2006 | Ismagilov et al. | |
| 7,708,949 B2 | 5/2010 | Stone et al. | |
| RE41,780 E | 9/2010 | Anderson et al. | |
| 8,273,573 B2 | 9/2012 | Ismagilov et al. | |
| 8,304,193 B2 | 11/2012 | Ismagilov et al. | |
| 8,329,407 B2 | 12/2012 | Ismagilov et al. | |
| 8,337,778 B2 | 12/2012 | Stone et al. | |
| 8,658,430 B2 | 2/2014 | Miller et al. | |
| 8,765,485 B2 | 7/2014 | Link et al. | |
| 8,822,148 B2 | 9/2014 | Ismagliov | |
| 8,835,358 B2 | 9/2014 | Fodor et al. | |
| 8,889,083 B2 | 11/2014 | Ismagilov et al. | |
| 9,089,844 B2 | 7/2015 | Hiddessen et al. | |
| 9,126,160 B2 | 9/2015 | Ness et al. | |
| 9,216,392 B2 | 12/2015 | Hindson et al. | |
| 9,290,808 B2 | 3/2016 | Fodor et al. | |
| 9,290,809 B2 | 3/2016 | Fodor et al. | |
| 9,315,857 B2 | 4/2016 | Fu et al. | |
| 9,347,059 B2 | 5/2016 | Saxonov | |
| 9,364,803 B2 | 6/2016 | Yurkovetsky et al. | |
| 9,388,465 B2 | 7/2016 | Hindson et al. | |
| 9,500,664 B2 | 11/2016 | Ness et al. | |
| 9,567,631 B2 | 2/2017 | Hindson et al. | |
| 9,567,645 B2 | 2/2017 | Fan et al. | |
| 9,567,646 B2 | 2/2017 | Fan et al. | |
| 9,598,736 B2 | 3/2017 | Fan et al. | |

(Continued)

FOREIGN PATENT DOCUMENTS

| | | |
|---|---|---|
| EP | 2047910 A2 | 4/2009 |
| WO | 0189788 A2 | 11/2001 |

(Continued)

OTHER PUBLICATIONS

Rothberg, et al., "An integrated semiconductor device enabling non-optical genome sequencing", Nature, vol. 475, pp. 348-352, Jul. 21, 2011.
Shimkus, et al., "A chemically cleavable biotinylated nucleotide: usefulness in the recovery of protein-DNA complexes from avidin affinity columns.", Proc Natl Acad Sci U S A., vol. 82, No. 9, pp. 2593-2597, May 1985.
Song, et al., "A Microfluidic System for Controlling Reaction Networks in Time", Angew. Chem. Int. Ed. 2003, vol. 42, No. 7, pp. 767-772, , Received: Sep. 6, 2002.
Soumillon, et al., "Characterization of Directed Differentiation by High-Throughput Single-Cell RNA-Seq", BioRxiv, pp. 1-13, Preprint: Mar. 5, 2014.
Spies, et al., "Genome-wide reconstruction of complex structural variants using read clouds", Nat Methods, vol. 14, No. 9, pp. 915-920, Sep. 2017.

(Continued)

*Primary Examiner* — Richard A Schnizer
(74) *Attorney, Agent, or Firm* — Johnson, Marcou, Isaacs & Nix, LLC; F. Brent Nix Esq.; Michael B. Scher Esq.

(57) ABSTRACT

The application relates to proteome analysis in single cells. Specifically, disclosed are high throughput methods of detecting proteins in single cells using barcoding, aptamers and single cell sequencing. Solid supports used in recording the cell-of-origin of target proteins and target proteins expressed in the cell-of-origin are disclosed. Additionally, methods of detecting proteins and mRNA in single cells are disclosed. Additionally, methods of detecting protein interactions are disclosed. Additionally, methods of detecting post translationally modified proteins in single cells are disclosed. The application also relates to solid supports or beads and methods of producing said solid supports or beads for use in the described methods.

35 Claims, 3 Drawing Sheets

(56) References Cited

U.S. PATENT DOCUMENTS

| | | | |
|---|---|---|---|
| 9,636,682 B2 | 5/2017 | Hiddessen et al. | |
| 9,637,799 B2 | 5/2017 | Fan et al. | |
| 9,644,204 B2 | 5/2017 | Hindson et al. | |
| 9,649,635 B2 | 5/2017 | Hiddessen et al. | |
| 9,689,024 B2 | 6/2017 | Hindson et al. | |
| 9,695,468 B2 | 7/2017 | Hindson et al. | |
| 9,708,654 B2 | 7/2017 | Hunicke-Smith et al. | |
| 9,708,659 B2 | 7/2017 | Fodor et al. | |
| 9,816,121 B2 | 11/2017 | Agresti et al. | |
| 9,816,137 B2 | 11/2017 | Fodor et al. | |
| 9,826,137 B2 | 11/2017 | Yokomizo | |
| 9,845,502 B2 | 12/2017 | Fodor et al. | |
| 9,856,530 B2 | 1/2018 | Hindson et al. | |
| 9,885,034 B2 | 2/2018 | Saxonov | |
| 2002/0172965 A1 | 11/2002 | Kamb et al. | |
| 2005/0172476 A1 | 8/2005 | Stone et al. | |
| 2006/0163385 A1 | 7/2006 | Link et al. | |
| 2007/0003442 A1 | 1/2007 | Link et al. | |
| 2007/0184489 A1 | 8/2007 | Griffiths et al. | |
| 2007/0195127 A1 | 8/2007 | Ahn et al. | |
| 2008/0003142 A1 | 1/2008 | Link et al. | |
| 2008/0014589 A1 | 1/2008 | Link et al. | |
| 2009/0005254 A1 | 1/2009 | Griffiths et al. | |
| 2009/0042737 A1 | 2/2009 | Katz et al. | |
| 2009/0131543 A1 | 5/2009 | Weitz et al. | |
| 2010/0002241 A1 | 1/2010 | Hirose | |
| 2010/0022414 A1 | 1/2010 | Link et al. | |
| 2010/0136544 A1 | 6/2010 | Agresti et al. | |
| 2010/0137163 A1 | 6/2010 | Link et al. | |
| 2010/0172803 A1 | 7/2010 | Stone et al. | |
| 2010/0298152 A1* | 11/2010 | Brown | C12N 15/111 506/4 |
| 2011/0265198 A1 | 10/2011 | Gregory et al. | |
| 2011/0319298 A1 | 12/2011 | Benner et al. | |
| 2012/0017290 A1 | 1/2012 | Cui et al. | |
| 2012/0122714 A1 | 5/2012 | Samuels et al. | |
| 2012/0219947 A1 | 8/2012 | Yurkovetsky et al. | |
| 2012/0220494 A1 | 8/2012 | Samuels et al. | |
| 2013/0236946 A1 | 9/2013 | Gouble | |
| 2013/0274117 A1 | 10/2013 | Church et al. | |
| 2014/0155295 A1 | 6/2014 | Hindson et al. | |
| 2014/0199730 A1 | 7/2014 | Agresti et al. | |
| 2014/0199731 A1 | 7/2014 | Agresti et al. | |
| 2014/0235506 A1 | 8/2014 | Hindson et al. | |
| 2014/0256595 A1 | 9/2014 | Link et al. | |
| 2014/0357500 A1 | 12/2014 | Vigneault et al. | |
| 2015/0005199 A1 | 1/2015 | Hindson et al. | |
| 2015/0011430 A1 | 1/2015 | Saxonov | |
| 2018/0030515 A1 | 2/2018 | Regev et al. | |
| 2018/0320224 A1 | 11/2018 | Gaublomme et al. | |

FOREIGN PATENT DOCUMENTS

| | | |
|---|---|---|
| WO | 02099078 A2 | 12/2002 |
| WO | 2004002627 A2 | 1/2004 |
| WO | 2004016767 A2 | 2/2004 |
| WO | 2004091763 A2 | 10/2004 |
| WO | 2005003291 A2 | 1/2005 |
| WO | 2005021151 A1 | 3/2005 |
| WO | 2006040551 A2 | 4/2006 |
| WO | 2006040554 A1 | 4/2006 |
| WO | 2006096571 A2 | 9/2006 |
| WO | 2007081385 A2 | 7/2007 |
| WO | 2007089541 A2 | 8/2007 |
| WO | 2007133710 A2 | 11/2007 |
| WO | 2008063227 A2 | 5/2008 |
| WO | 2009012418 A2 | 1/2009 |
| WO | 2009036379 A2 | 3/2009 |
| WO | 2011079176 A2 | 6/2011 |
| WO | 2013188872 A1 | 12/2013 |
| WO | 2014026032 A2 | 2/2014 |
| WO | 2014047556 A1 | 3/2014 |
| WO | 2014047561 A1 | 3/2014 |
| WO | 2014085802 A1 | 6/2014 |
| WO | 2014093622 A2 | 6/2014 |
| WO | 2014143158 A1 | 9/2014 |
| WO | 2014204723 A1 | 12/2014 |
| WO | 2014204726 A1 | 12/2014 |
| WO | 2014204727 A1 | 12/2014 |
| WO | 2014210353 A2 | 12/2014 |
| WO | 2015161177 A1 | 10/2015 |
| WO | 2015164212 A1 | 10/2015 |
| WO | 2016040476 A1 | 3/2016 |
| WO | 2016049251 A1 | 3/2016 |
| WO | 2016100976 A2 | 6/2016 |
| WO | 2016168584 A1 | 10/2016 |
| WO | 2017075265 A1 | 5/2017 |
| WO | 2017075292 A1 | 5/2017 |
| WO | 2017075294 A1 | 5/2017 |
| WO | 2017164936 A1 | 9/2017 |

OTHER PUBLICATIONS

Stoeckius, et al., "Large-scale simultaneous measurement of epitopes and transcriptomes in single cells", Nature Methods, vol. 14, No. 9, pp. 865-868, Sep. 2017.

Taylor, et al., "A scalable high-throughput method for RNA-Seq analysis of thousands of single cells", illumina I Bio-Rad, 2016.

Tewhey, et al., "Microdroplet-based PCR enrichment for large-scale targeted sequencing", Nature Biotechnology, vol. 27, No. 11, pp. 1025-1031, Nov. 1, 2009.

The Broad Institute, Inc., "Communication Pursuant to Rule 164(2)(b) and Article 94(3) EPC", Jul. 11, 2018, 12 pages.

Tice, et al., "Formation of Droplets and Mixing in Multiphase Microfluidics at Low Values of the Reynolds and the Capillary Numbers", Langmuir, vol. 19, No. 22, pp. 9127-9132, Published on Web: Aug. 12, 2003.

Wilson, "Ape1 abasic endonuclease activity is regulated by magnesium and potassium concentrations and is robust on alternative DNA structures.", J Mol Biol., vol. 345, No. 5, pp. 1003-1014, Feb. 4, 2005.

Wu, et al., "Termination of DNA synthesis by N6-alkylated, not 3'-0-alkylated, photocleavable 2'-deoxyadenosine triphosphates", Nucleic Acids Res., vol. 35, No. 19, pp. 6339-6349, Sep. 18, 2007.

Yan, et al., "Intestinal enteroendocrine lineage cells possess homeostatic and injury-inducible stem cell activity", Cell Stem Cell, vol. 21, No. 1, pp. 78-90, Jul. 6, 2017.

Yan, et al., "Non-equivalence of Wnt and R-spondin ligands during Lgr5+ intestinal stem cell self-renewal", Nature, vol. 545, No. 7653, pp. 238-242, May 11, 2017.

Zhang, et al., "Massively Parallel Single-Molecule and Single-Cell Emulsion Reverse Transcription Polymerase Chain Reaction Using Agarose Droplet Microfluidics", Anal. Chem., vol. 84, No. 8, pp. 3599-3606, Published: Mar. 27, 2012.

Zheng, et al., "Massively parallel digital transcriptional profiling of single cells", Nature Communications, vol. 8, Article No. 14049, pp. 1-12, Published: Jan. 16, 2017.

Metzker, "Sequencing technologies—the next generation", Nature Reviews, Genetics, vol. 11, pp. 31-46, Published online: Dec. 8, 2009.

Klein, et al., "Droplet Barcoding for Single-Cell Transcriptomics Applied to Embryonic Stem Cells", Cell, vol. 161, No. 5, May 21, 2015, 1187-1201.

Rohloff, et al., "Nucleic Acid Ligands With Protein-like Side Chains: Modified Aptamers and Their Use as Diagnostic and Therapeutic Agents", Molecular Therapy Nucleic Acids, vol. 3, No. 10, Oct. 7, 2014, 13 pages.

"2017 Top 10 Innovations", 2017 Top 10 Innovations, The Scientist, pp. 1-11, Dec. 1, 2017.

"Acrylamide Product Information Sheet", Sigma Aldrich 1996 Product Information Sheet, A8887, pp. 1-2, 1996.

"American Cell Biology Meeting Program 2017", The 2017 ASCB EMBO Meeting, pp. 1-198, Dec. 2017.

"An Introduction to Linked-Read Technology for a More Comprehensive Genome and Exome Analysis", 10X Genomics Technical Note, pp. 1-5, 2016.

(56) References Cited

OTHER PUBLICATIONS

Bio-Rad and Illumina to Co-Develop Comprehensive Solution for Single-Cell Genomics, "Scalable, High-Throughput Platform to Offer Unprecedented Insight into Gene Expression of Individual Cells," Bio-Rad Newsroom, pp. 1-2, Jan. 11, 2016.
"Bio-Rad ddSEQ Single-Cell Isolator Instruction Manual", Bio-Rad, Catalog #12004336, pp. 1-24, 2017.
"Bio-Rad Laboratories, Inc. Form 10-K for the year ended Dec. 31, 2016", pp. 1-92.
"Bio-Rad Life Science Research Product Catalog", Bio-Rad Life Science Research 2017 Product Catalog, pp. 1-500, 2017.
"Boston Medical Center/ Boston University School of Medicine Department of Medicine Newsletter", pp. 1-20, 2017.
"Cancer Moonshot", National Cancer Institute, pp. 1-4, Jan. 8, 2019.
"ChromiumTM Genome Reagent Kits v2 User Guide," Multiplex Kit, 96 rxns, PN-120262, 10X Genomics, pp. 1-71, 2016.
"ChromiumTM Single Cell 3' Reagent Kits Quick Reference Cards", ChromiumTM Single Cell 3' Chip Kit PN-120232, 10X Genomics, pp. 1-10, 2016.
"ChromiumTM Chromium Single Cell 3' Reagent Kits Safety Data Sheets", ChromiumTM Single Cell 3' Gel Bead Kit PN-120231, 10X Genomics, pp. 1-10, Jul. 11, 2016.
"ChromiumTM Chromium Single Cell 3' Reagent Kits v2 Safety Data Sheets," Chromium Single Cell 3' Gel Bead Kit v2, 16 runs, PN-120235, 10X Genomics, pp. 1-10, Oct. 7, 2016.
"Chromium Single Cell 3' Reagent Kits v3 with Feature Barcoding technology for CRISPR Screening", Chromium Single Cell 3' GEM, Library & Gel Bead Kit v3, 4 rxns PN-1000092, 10X Genomics, pp. 1-70, CG000184 | Rev A, 2018.
"ChromiumTM Single Cell 3' Reagent Kits v2 Quick Reference Cards," ChromiumTM Single Cell 3' Library & Gel Bead Kit, 4 rxns PN-120267, 10X Genomics, CG000075 | Rev C, pp. 1-10, 2017.
"ChromiumTM Single Cell 3' Reagent Kits Safety Data Sheets," ChromiumTM Single Cell 3' Library Kit, 10X Genomics, PN-120230, pp. 1-139, May 25, 2016.
"ChromiumTM Single Cell 3' Reagent Kits v2 Safety Data Sheets," ChromiumTM Single Cell 3' Library Kit v2 16 rxns, PN-120234, 10X Genomics, pp. 1-121, Oct. 7, 2016.
"Chromium Single Cell 3' Reagent Kits v2 User Guide," Chromium Single Cell 3' Library & Gel Bead Kit v2, 16 rxns PN-120237, 10X Genomics, pp. 1-74, 2018.
"ChromiumTM Single Cell V(D)J Reagent Kits User Guide," ChromiumTM Single Cell 5' Library & Gel Bead Kit, 16 rxns PN-1000006, 10X Genomics, pp. 1-73, 2017.
"Chromium Single Cell 3' Reagent Kits v2 User Guide", Chromium Single Cell A Chip Kit, 16 rxns PN-1000009, 10X Genomics, pp. 1-74, CG00052 | Rev E, 2018.
"Chromium Single Cell 3' Reagent Kits v2 Safety Data Sheets," Chromium Single Cell A Chip Kit, 48 runs, 10X Genomics, PN-120236, Oct. 6, 2016.
"Chromium Single Cell ATAC Reagent Kits," Chromium Single Cell ATAC Library & Gel Bead Kit, 16 rxns PN-1000110, 10X Genomics, CG000168 | Rev A, pp. 1-47, 2018.
"Chromium Single Cell DNA Reagent Kits", Chromium Single Cell DNA Library & Gel Bead Kit, 16 rxns PN-1000040, 10X Genomics, CG000153 | Rev B, pp. 1-65, 2018.
"ChromiumTM Controller Training Kit User Guide", 10X Genomics, CG00021 | Rev B, pp. 1-27, (Product ID 120244), 2016.
"ChromiumTM Training Kits Safety Data Sheets", ChromiumTM Training Reagents and Gel Bead Kit, 10X Genomics, PN-120238, Rev A, pp. 1-33, May 24, 2016.
"ddSEQ™ Cartridge Holder", Bio-Rad ddSEQ™ Cartridge Holder #12004739, 2016.
"ddSEQ™ Single-Cell Isolator—Accessories", ddSEQ™ Single-Cell Isolator—Accessories—Bio-Rad, pp. 1-2, 2016.
"ddSEQ™ Single-Cell Isolator—Ordering", ddSEQ™ Single-Cell Isolator Bio-Rad, 2016.
"ddSEQ™ Single-Cell Isolator by Bio-Rad", Bio-Rad, pp. 1-8, Select Science, 2019.
"ddSEQ™ Single-Cell Isolator by Bio-Rad", ddSEQ™ Single-Cell Isolator, Bio-Rad, pp. 1-2, 2016.
"ddSEQ™ Test Cartridges", Bio-Rad ddSEQ™ Test Cartridges #12003862, 2016.
"Deoxyribonuclease I from bovine pancreas", Sigma-Aldrich Deoxyribonuclease I from bovine pancreas, CAS No. 9003-98-9, 2018.
"DNase I (RNase-free)", New England Biolabs, Inc. (NEB), pp. 1-6, 2018.
"DTT 1,4-Dithiothreitol", Sigma-Aldrich, CAS No. 3483-12-3, pp. 1-4, 2015.
Office Action issued by the European Patent Office in Application No. 15767655.2 dated Apr. 17, 2018, 4 pages.
Office Action issued by the European Patent Office in Application No. 15767655.2 dated Jul. 11, 2018, 12 pages.
Banga, J.P., "SDS-Polyacrylamide Gel Electrophoresis (SDS-PAGE)", Encyclopedia of Immunology ISBN:0-12-226765-6, pp. 2143-2144, 1998.
"Generation of Human Tumor Atlases-Cancer Moonshot Recommendation", National Cancer Institute, pp. 1-4, Jan. 8, 2019.
"Genome Analysis Core", pp. 1-2, Georgia Institute of Technology, 2019.
"Georgia Tech—Shared User Management System", pp. 1-12, Georgia Institute of Technology, 2015.
"Hydrophobic Interaction Chromatography", Amersham Pharmacia Biotech 2000, Edition AB, pp. 1-104, ISBN 91-970490-4-2, 2000.
"Illumina and Bio-Rad Launch Solution for Single-Cell Genomic Sequencing to Enable Robust Study of Complex Diseases", Bio-Rad, pp. 1-2, Jan. 9, 2017.
"Illumina and Bio-Rad Launch Solution for Single-Cell Genomic Sequencing to Enable Robust Study of Complex Diseases", 69th AACC Annual Scientific Meeting Press Program, Article ID: 678428, pp. 1-6, Jul. 25, 2017.
"Illumina Bio-Rad SureCell WTA 3' Library Prep Reference Guide", Illumina, Document # 1000000021452 v01, pp. 1-53, Jun. 2017.
"Illumina SureCell WTA 3' Checklist", Illumina, Document # 1000000021454 v00, pp. 1-6, Feb. 2017.
"Illumina® | Bio-Rad® Single Cell Sequencing", illumina I Bio-Rad, pp. 1-37, 2015.
"Illumina® Bio-Rad® SureCellTM WTA 3' Library Prep Kit for the ddSEQTM System", illumina I Bio-Rad, pp. 1-4, 2015.
"Infoporte—Cores", Infoporte I Version: 7.1.1 | © 2019 The University of North Carolina at Chapel Hill.
"The Instrument—Chromium Controller Compatible Solutions", 10X Genomics, pp. 1-7, 2019.
Chung, et al., "Statistical Significance of Variables Driving Systematic Variation in High-Dimensional Data", Bioinformatics, vol. 31, No. 4, pp. 545-554, Advance Access publication: Oct. 21, 2014.
Collins, "Biomedical Research Highlighted in Science's 2018 Breakthroughs", NIH Director's Blog, pp. 1-9, Jan. 8, 2019.
Corbo, et al., "A Typology of Photoreceptor Gene Expression Patterns in the Mouse", PNAS, vol. 104, Issue 29, pp. 12069-12074, Jul. 17, 2007.
Cuatrecasas, Pedro, "Protein Purification by Affinity Chromatography", J Biol Chem, vol. 245, Issue 12, pp. 3059-3065, Jun. 25, 1970.
Damha, et al., "An improved procedure for derivatization of controlled-pore glass beads for solid-phase oligonucleotide synthesis", Nucleic Acids Res., vol. 18, No. 13, pp. 3813-3821, Accepted: May 17, 1990.
Descamps, et al., "Gelatinase B/matrix Metalloproteinase-9 Pprovokes Cataract by Cleaving Lens BetaB 1 Crystallin", The FASEB Journal, vol. 19, Issue 1, pp. 29-35, Jan. 2005.
Dixit, et al., "Perturb-Seq: Dissecting Molecular Circuits with Scalable Single-Cell RNA Profiling of Pooled Genetic Screens", Cell, vol. 167, Issue 7, pp. 1853-1866, Dec. 15, 2016.
Dobin, et al., "STAR: Ultrafast Universal RNA-seq Aligner", Bioinformatics, vol. 29, Issue 1, pp. 15-21, Advance Access publication: Oct. 25, 2012.
Dressman, et al., "Transforming single DNA molecules into fluorescent magnetic particles for detection and enumeration of genetic variations", PNAS, vol. 100, No. 15, pp. 8817-8822, Jul. 22, 2003.

(56) References Cited

OTHER PUBLICATIONS

Droege, et al., "The Genome Sequencer FLX System—longer reads, more applications, straight forward bioinformatics and more complete data sets.", J Biotechnol., vol. 136, Issues 1-2, pp. 3-10, Accepted: Mar. 31, 2008.
Edd, et al., "Controlled Encapsulation of Single Cells into Monodisperse Picoliter Drops", Lab Chip, vol. 8, Issue 8, pp. 1262-1264, Aug. 2008.
Ester, et al., "A Density-Based Algorithm for Discovering Clusters in Large Spatial Databases with Noise", pp. 226-231, KDD-96, 1996.
Farmer, et al., "Defining epithelial cell dynamics and lineage relationships in the developing lacrimal gland", Development, The Company of Biologists, vol. 144, Issue 13, pp. 2517-2528, Accepted: May 31, 2017.
Feigenspan, et al., "Expression of Neuronal Connexin36 in All Amacrine Cells of the Mammalian Retina", The Journal of Neuroscience, vol. 21, Issue 1, pp. 230-239, Jan. 1, 2001.
Gao, et al., "Secondary structure effects on DNA hybridization kinetics: a solution versus surface comparison", Nucleic Acids Research, 2006, vol. 34, No. 11, pp. 3370-3377, Accepted: May 27, 2006.
Glatthar, et al., "A New Photocleavable Linker in Solid-Phase Chemistry for Ether Cleavage", Org. Lett. 2000, vol. 2, No. 15, pp. 2315-2317, Received: May 18, 2000.
Greenfieldboyce, "Biological cartographers seek to map the trillions of cells in the human body", NPR, pp. 1-5, Jan. 5, 2019.
Greer, et al., "Linked read sequencing resolves complex genomic rearrangements in gastric cancer metastases", Genome Medicine, vol. 9, No. 57, pates 1-17, 2017.
Gueroult, et al., "How Cations Can Assist DNase I in DNA Binding and Hydrolysis", PLoS Comput Biol., vol. 6, Issue 11:e1001000, pp. 1-11, Nov. 18, 2010.
Haber, et al., "A single-cell survey of the small intestinal epithelium", Nature, vol. 551, No. 7680, pp. 333-339, Nov. 16, 2017.
Hamady, et al., "Error-correcting barcoded primers for pyrosequencing hundreds of samples in multiplex", Nature Methods, vol. 5, No. 3, pp. 235-237, Mar. 2008.
Hamady, et al., "Microbial community profiling for human microbiome projects: Tools, techniques, and challenges", Genome Res., vol. 19, No. 7, pp. 1141-1152, ISSN 1088-9051/09, Jul. 2009.
He, et al., "High-resolution crystal structures reveal plasticity in the metal binding site of apurinic/apyrimidinic endonuclease I.", Biochemistry, vol. 53, No. 41, pp. 6520-6529, Published: Sep. 24, 2014.
Hoffmann, et al., "DNA bar coding and pyrosequencing to identify rare HIV drug resistance mutations", Nucleic Acids Res., vol. 35, No. 13, e91, pp. 1-8, Published online: Jun. 18, 2007.
Holmberg, et al., "The biotin-streptavidin interaction can be reversibly broken using water at elevated temperatures.", Electrophoresis, vol. 26, No. 3, pp. 501-510, Feb. 2005.
Islam, et al., "Quantitative single-cell RNA-seq with unique molecular identifiers", Nature Methods, vol. 11, No. 2, pp. 163-166, Feb. 2014.
Kaiser, et al., "Huge trove of British biodata is unlocking secrets of depression, sexual orientation, and more", Science | AAAS, pp. 1-12, Jan. 3, 2019.
Kovall, et al., "Structural, functional, and evolutionary relationships between exonuclease and the type II restriction endonucleases", Proc Natl Acad Sci U S A., vol. 95, No. 14, pp. 7893-7897, Jul. 1998.
Kumaresan, et al., "High-Throughput Single Copy DNA Amplification and Cell Analysis in Engineered Nanoliter Droplets", Anal. Chem., vol. 80, No. 10, pp. 3522-3529, May 15, 2008.
Kutnjak, et al., "Calorimetric study of octylcyanobiphenyl liquid crystal confined to a controlled-pore glass.", Physical Review E, The American Physical Society, pp. 021705-1-021705-12, Published: Aug. 22, 2003.
Litosh, et al., "Improved nucleotide selectivity and termination of 3'-OH unblocked reversible terminators by molecular tuning of 2-nitrobenzyl alkylated HOMedU triphosphates.", Nucleic Acids Res., vol. 39, No. 6, pp. 1-13, Published online: Jan. 11, 2011.
Macosko, et al., "Highly Parallel Genome-Wide Expression Profiling of Individual Cells Using Nanoliter Droplets", Cell, vol. 161, No. 5, pp. 1202-1214, May 21, 2015.
Malone, et al., "Bringing Renal Biopsy Interpretation Into the Molecular Age With Single-Cell RNA Sequencing", Seminars in Nephrology, vol. 38, Issue 1, pp. 1-17, Author Manuscript; available in PMC: Jan. 1, 2019.
Margulies, et al., "Genome Sequencing in Open Microfabricated High Density Picoliter Reactors", Nature, vol. 437, No. 7057, pp. 376-380, Sep. 15, 2005.
Mckenna, et al., "The Macaque Gut Microbiome in Health, Lentiviral Infection, and Chronic Enterocolitis", PLoS Pathog., vol. 4, Issue 2, e20, pp. 0001-0012, Feb. 8, 2008.
Metzker, "Emerging technologies in DNA sequencing.", Genome Res., vol. 15, No. 12, pp. 1767-1776, Dec. 2005.
Miller, et al., "Basic Concepts of Microarrays and Potential Applications in Clinical Microbiology", Clinical Microbiology Reviews, vol. 22, No. 4, pp. 611-633, Oct. 2009.
Mol, et al., "DNA-bound structures and mutants reveal abasic DNA binding by APE1 and DNA repair coordination.", Nature, vol. 403, No. 6768, pp. 451-456, Jan. 27, 2000.
Narasimhan, et al., "Health and population effects of rare gene knockouts in adult humans with related parents", Science, vol. 352, No. 6284, pp. 474-477, Apr. 22, 2016.
Nguyen, "Optical detection for droplet size control in microfluidic droplet-based analysis systems", Nguyen et al., Optical detection for droplet size control in microfluidic droplet-based analysis systems, 117 Sensors and Actuators B 117, pp. 431-436, Available online: Jan. 18, 2006.
Novak, et al., "Single cell multiplex gene detection and sequencing with microfluidically generated agarose emulsions", Angew. Chem. Int. Ed., pp. 1-11, 2010.
Novak, et al., "Single Cell Multiplex Gene Detection and Sequencing with Microfluidically Generated Agarose Emulsions", Agnew. Chem. Int. Ed., pp. 390-395, Jan. 10, 2011.
Pal, et al., "Construction of developmental lineage relationships in the mouse mammary gland by single-cell RNA profiling", Nature Communications, vol. 8, Article No. 1627, pp. 1-14, Nov. 20, 2017.
Parameswaran, et al., "A pyrosequencing-tailored nucleotide barcode design unveils opportunities for large-scale sample multiplexing", Nucleic Acids Res., vol. 35, No. 19, e130, pp. 1-9, Published online: Oct. 11, 2007.
Pennisi, "Development Cell by Cell", Science, vol. 362, Issue 6421, pp. 1344-1345, Dec. 21, 2018.
Perona, "Type II restriction endonucleases.", Methods, vol. 28, No. 3, pp. 353-364, Accepted: Jul. 30, 2002.
Peterson, et al., "The effect of surface probe density on DNA hybridization", Nucleic Acids Res., vol. 29, No. 24, pp. 5163-5168, Dec. 15, 2001.
Qi, et al., "Digital analysis of the expression levels of multiple colorectal cancer-related genes by multiplexed digital-PCR coupled with hydrogel bead-array.", Analyst, vol. 136, No. 11, pp. 2252-2259, Accepted: Mar. 11, 2011.
Final Office Action for U.S. Appl. No. 15/453,405, issued by the U.S. Patent Office dated Mar. 27, 2019, 17 pages.
"Markman Order In re Certain Microfluidic Systems and Components Thereof and Products Containing Same", Docket Alarm, pp. 1-6, Oct. 31, 2018.
"Molecular and Genomics Core Facility Equipment", Molecular and Genomics Core Facility, pp. 1-7, 2018.
"N,N'-Methylenebis(acrylamide)", 146072 Sigma-Aldrich, CAS No. 110-26-9, 2018.
"Neuroscience 2017 Program", Society for Neuroscience, pp. 1-2, 2017.
"Notice of Intent to Certify Sole Source", Sole Source Certification No. SS5098 for Bio-Rad ddSeq Single Cell Isolation System and associated accessories, pp. 1-5, Jun. 5, 2017.
"Nucleic Acid Sample Preparation for Downstream Analyses", GE Healthcare Life Sciences Manual, pp. 1-168, 2009.
"Omniscript Reverse Transcription Handbook", Qiagen, pp. 1-32, Oct. 2010.

(56) References Cited

OTHER PUBLICATIONS

"Phosphate-buffered saline (PBS)", pdb.rec8247-, Cold Spring Harbor Protocols (2006).
"Powerful New Tool for Genome Analysis", Georgia Tech Bioinformatics, pp. 1-3, Nov. 14, 2017.
"Q Sepharose High Performance SP Sepharose High Performance", GE Healthcare, Data File 18-1172-88 AB, pp. 1-8, Apr. 2006.
"Research Highlights: Human Cell Atlas", Human Cell Atlas | Broad Institute, pp. 1-4, Jan. 8, 2019.
"Restriction Endonucleases Technical Guide", BioLabs Inc., pp. 1-24, Aug. 2015.
"Reverse Transcription Reaction Setup—Seven Important Considerations", ThermoFisher Scientific, pp. 1-15, 2018.
"Sequencing Power for Every Scale Systems for every application. For every lab.", Illumina, pp. 1-70, 2016.
"Single-Cell RNA Data Analysis Workflow RNA analysis from single cells using the Illumina Bio-Rad Single-Cell Sequencing Solution with the BaseSpace® SureCellTM RNA Single-Cell App.", illumina | Bio-Rad, pp. 1-4, 2017.
"Single-cell RNAseq (Biorad/Illumina ddSEQ)", UNC School of Medicine, pp. 1-3, 2018.
"SITC 2017 Scientific Highlights—Nov. 11", The Sentinel—The Official Blog of the Society for Immunotherapy of Cancer (SITC)., pp. 1-4, Nov. 12, 2017.
"SureCell WTA 3' Library Prep Kit Support, Questions & Answers", Illumina, pp. 1-4, 2019.
"SureCell WTA 3' Library Prep Kit for the ddSEQ System", Ilumina, pp. 1-6, 2019.
"The Illumina Bio-Rad Single Cell Sequencing Solution", illumina | Bio-Rad, pp. 1-3, 2018.
"The Illumina Bio-Rad Single-Cell Sequencing Solution Robust and scalable single-cell sequencing", illumina | Bio-Rad, pp. 1-4, 2016.
"Top 10 Innovations 2015", The Scientist, pp. 1-12, Dec. 1, 2015.
"Transcriptor Reverse Transcriptase", Roche, Ver. 13, pp. 1-13, Jun. 2017.
"Types of Restriction Endonucleases", pp. 1-2, 2018.
U.S. Office Action issued in copending U.S. Appl. No. 15/453,405, filed Aug. 28, 2018, dated Aug. 28, 2018, 16 pages.
"University of Mississippi Medical Center, Molecular and Genomics Core Facility, Service Home", pp. 1-2, 2018.
"Genomics Resources Core Facility", Weill Cornell Medicine, pp. 1-5, 2018.
Abate, et al., "Beating Poisson encapsulation statistics using close-packed ordering", Lab Chip, vol. 9, pp. 2628-2631, Accepted: Jul. 24, 2009.
Adamson, et al., "A multiplexed single-cell CRISPR screening platform enables systematic dissection of the unfolded protein response", Cell., vol. 167, Issue 7, pp. 1867-18822, Dec. 15, 2016.
International Search Report and Written Opinion issued in International Application No. PCT/US2015/049178, dated Feb. 22, 2016, 18 pages.
Andersen, et al., "A Quantitative Study of the Human Cerebellum with Unbiased Stereological Techniques", The Journal of comparative neurology, vol. 326, Issue 4, pp. 549-560, Dec. 22, 1992.
Ascoli, et al., "Petilla Terminology: Nomenclature of Features of GABAergic Interneurons of the Cerebral Cortex", Nature reviews Neuroscience, vol. 9, pp. 557-568, Jul. 2008.

International Preliminary Report on Patentability issues in International Application No. PCT/US2015/049178, dated Mar. 23, 2017, 12 pages.
Barany, Francis, "Genetic Disease Detection and DNA Amplification Using Cloned Thermostable Ligase", PNAS, vol. 88, Issue 1, pp. 189-193, Jan. 1991.
Barany, Francis, "The Ligase Chain Reaction in a PCR World", PCR Methods and Applications, vol. 1, pp. 5-16, 1991.
Bar-Joseph, et al., "Genome-Wide Transcriptional Analysis of the Human Cell Cycle Identifies Genes Differentially Regulated in Normal and Cancer Cells", PNAS, vol. 105, Issue 3, pp. 955-960, Jan. 22, 2008.
Barres, et al., "Immunological, Morphological, and Electrophysiological Variation Among Retinal Ganglion Cells Purified by Panning", Neuron, vol. 1, Issue 9, pp. 791-803, Nov. 1988.
Beer, et al., "On-Chip Single-Copy Real-Time Reverse-Transcription PCR in Isolated Picoliter Droplets", Analytical Chemistry, vol. 80, Issue 6, pp. 1854-1858, Mar. 15, 2008.
Bentley, et al., "Accurate whole human genome sequencing using reversible terminator chemistry.", Nature, 456 (7218), pp. 53-59, Nov. 6, 2008.
Berman, et al., "Mapping the Stereotyped Behaviour of Free Moving Fruit Flies", Journal of the Royal Society Interface, vol. 11, Issue 99, 20140672, pp. 1-12, Aug. 20, 2014.
Binladen, et al., "The Use of Coded PCR Primers Enables High-Throughput Sequencing of Multiple Homolog Amplification Products by 454 Parallel Sequencing", PLoS One; vol. 2, Issue 2: e197, pp. 1-9, Feb. 14, 2007.
Bitinaite, et al., "USER™ friendly DNA engineering and cloning method by uracil excision", Nucleic Acids Res. , vol. 35, No. 6, pp. 1992-2002, Publised online Mar. 6, 2007.
Black, Chris, "The ChromiumTM System: Linked Read and Single Cell RNA-Seq Applications Powered By GemCode Technology", 10X Genomics, pp. 1-57, Jul. 17, 2017.
Bochet, Christian G., "Photolabile protecting groups and linkers", J. Chem. Soc., Perkin Trans. 1, 2002,0, pp. 125-142, First published as an Advance Article on the Web: Dec. 13, 2001.
Brennecke, et al., "Accounting for Technical Noise in Single-Cell RNA-seq Experiments", Nature methods, vol. 10, Issue 11, 1093-1095, Sep. 22, 2013.
Bringer, et al., "Microfluidic Systems for Chemical Kinetics that Rely on Chaotic Mixing in Droplets", Philosophical Transactions of The Royal Society A Mathematical Physical and Engineering Sciences, vol. 362, Issue 1818, pp. 1087-1104, Jun. 2004.
Britten, et al., "Repeated Sequences in DNA. Hundreds of Thousands of Copies of DNA Sequences have been Incorporated into the Genomes of Higher Organisms", Science, vol. 161, Issue 3841, pp. 529-540, Aug. 9, 1968.
Brouzes, et al., "Droplet Microfluidic Technology for Single-Cell High-Throughput Screening", Proceedings of the National Academy of Sciences, vol. 106, No. 34, pp. 14195-14200, Aug. 25, 2009.
Brown, et al., "Chemical Synthesis and Cloning of a Tyrosine tRNA Gene", Methods in Enzymology, vol. 68, pp. 109-151, 1979.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, pp. 155-160, Feb. 2015.
Ding, et al., "Progress Towards a Systematic Comparison of Single Cell RNA-Seq Methods", Stanley Center for Psychiatric Research at Broad Institute, Klarman Cell Observatory at Broad Institute, Feb. 12, 2019, 1 page.

\* cited by examiner

FIG. 1A
FIG. 1B
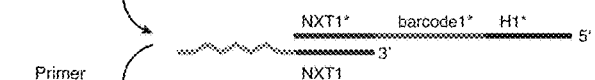
FIG. 1C
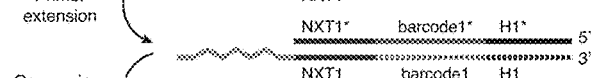
FIG. 1D
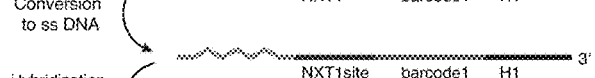
FIG. 1E
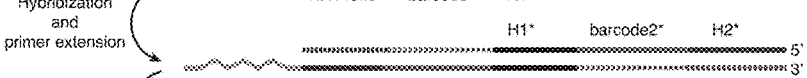
FIG. 1F
FIG. 1G
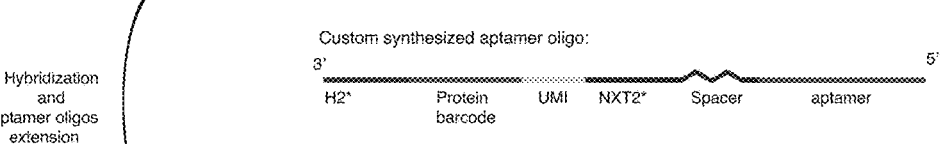
FIG. 1H
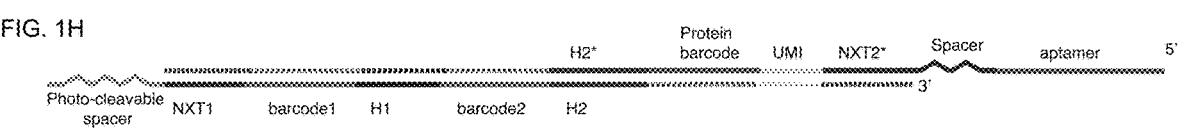
FIG. 1A-1H

SINGLE-CELL PROTEOMIC ASSAY USING APTAMERS

CROSS-REFERENCE TO RELATED APPLICATIONS

This application claims the benefit of U.S. Provisional Application No. 62/500,784, filed May 3, 2017. The entire contents of the above-identified application are hereby fully incorporated herein by reference.

STATEMENT REGARDING FEDERALLY SPONSORED RESEARCH

This invention was made with government support under Grant No. HG006193 awarded by the National Institutes of Health. The government has certain rights in the invention.

TECHNICAL FIELD

The subject matter disclosed herein is generally directed to methods and apparatuses for single cell proteomics using a sequencing readout. Additionally, the subject matter is directed to methods and apparatuses for combined single cell proteomics and transcriptome analysis using a sequencing readout.

BACKGROUND

Single cell analysis of genomic variation and transcriptome heterogeneity allows for identification of factors influencing disease susceptibility, unraveling of intracellular regulatory networks and discovery of novel cell types. Despite their status as main mediators of biological functions, proteins are currently only read out a handful at a time, either due to spectral overlap of fluorescent tags in flow cytometry (Perfetto, et al., (2004) Nature reviews Immunology 4, 648-655) or limit in the number of available isotope tags in mass cytometry (Bendall, et al. (2011) Science 332, 687-696). Conversely, mass spectrometry (LC-MS/MS) allows quantitative analysis of entire proteomes, but deep analysis requires large amounts of protein/cells, and is limited in throughput (i.e. amount of cells that can be analyzed over a given time period). Thus, there is a need for methods and apparatuses for performing highly multiplexed analysis of proteins in single cells at a high throughput.

Citation or identification of any document in this application is not an admission that such document is available as prior art to the present invention.

SUMMARY

It is an objective of the present invention to provide for novel methods and tools for multiplex detection of protein expression in single cells. It is a further objective to determine multiplex protein expression in a plurality of single cells in a high throughput manner. It is another objective of the present invention to determine protein expression using a sequencing readout. It is another objective of the present invention to determine protein expression and gene expression in single cells. It is another object of the present invention to detect protein-protein interactions in a single cell using a sequencing readout. It is another object of the present invention to detect protein-RNA interactions in a single cell using a sequencing readout.

In one aspect, the present invention provides for an oligonucleotide-adorned solid support for the identification of proteins expressed in single cells, wherein said solid support comprises a plurality oligonucleotides, wherein each of said oligonucleotides comprise: a linker directly attached to the solid support; an identical sequence for use as a sequencing priming site; a uniform or near-uniform cell barcode sequence, wherein the uniform or near-uniform cell barcode sequence is the same across all oligonucleotides on said solid support, but varies among the oligonucleotides on any other individual solid support; a uniform or near-uniform target barcode sequence, wherein the uniform or near-uniform target barcode sequence is specific to an individual aptamer; and an aptamer specific to the target barcode sequence configured for binding to a target protein, wherein the solid support binds to a plurality of target proteins, and wherein the solid support comprises more than one copy of oligonucleotides specific for each of the plurality of target proteins. In an embodiment, the oligonucleotides may be attached to a solid support, such as a binding surface (e.g., the surface of a microwell or of a microbead) via a linkage, which may comprise any moiety, functionalization, or modification of the binding surface and/or oligonucleotide that facilitates the attachment of the oligonucleotide to the surface. In certain embodiments, the solid support is porous and the binding surface comprises the inner surfaces of a microwell surface or microbead. The copy number of oligonucleotides specific for different target proteins on said solid support may be varied, whereby the solid support comprises a desired ratio of aptamers. Each oligonucleotide may further comprise a Unique Molecular Identifier (UMI) which differs for each oligonucleotide. The oligonucleotide-adorned solid support may further comprise a spacer between the aptamer and the oligonucleotide strand conjugated to said aptamer, wherein the spacer functions as a blocking agent against DNA polymerase extension. Not being bound by a theory, production of the oligonucleotide may comprise hybridization of oligonucleotides followed by extension with DNA polymerase. The spacer may comprise an internal C3 spacer. The UMI may comprise 6 to 20 nucleotides in length. Each barcode may range from 4 to 100 nucleotides in length. The linker may be chemically-cleavable, enzymatically cleavable, or photocleavable. The aptamers may further comprise a photoreactive group configured to covalently link the aptamers to captured proteins upon experimentally defined illumination. As used herein, the term "experimentally defined illumination" refers to illumination that can be performed at a point of choice in a method of using said solid support, i.e. after aptamer target recognition has taken place and non-specific proteins are washed away. The oligonucleotides may further comprise a reverse priming site after the target barcode sequence, whereby by the cell and target barcodes may be amplified by PCR. In certain embodiments, a sequencing library may be amplified by T7 polymerase expression or by PCR, whereby PCR requires forward and reverse priming sites.

The solid support may be a bead. The bead may be a magnetic bead. The bead may be a deformable bead. The bead may be a hydrogel bead. The solid support may be a surface of a microwell. The surface may comprise a hydrogel surface.

In another aspect, the oligonucleotide-adorned solid support comprises oligonucleotides further comprising a 6 to 12 nucleotide universal hybridization sequence on the opposite DNA strand as the aptamer, wherein said universal hybridization sequence is complementary to a hybridization sequence linked a set of second oligonucleotide linked affinity reagents. The affinity reagents may comprise an aptamer, antibody or antibody fragment.

In another aspect, the oligonucleotide-adorned solid support comprises oligonucleotides further comprising a poly T sequence on the opposite DNA strand as the aptamer, whereby the oligonucleotides are configured to capture polyadenylated mRNA.

In another aspect, the oligonucleotide-adorned solid support further comprises a plurality of second oligonucleotides on said solid support, said second oligonucleotides comprising: a linker directly attached to the solid support; an identical sequence for use as a sequencing priming site; a uniform or near-uniform cell barcode sequence, wherein the uniform or near-uniform cell barcode sequence is the same across all oligonucleotides on said solid support, but varies among the oligonucleotides on any other individual solid supports; and an oligonucleotide redundant sequence for capturing polyadenylated mRNAs and priming reverse transcription, whereby the solid support is configured to bind proteins and mRNAs. The oligonucleotide sequence for capturing polyadenylated mRNAs and priming reverse transcription may be an oligo dT sequence. Each second oligonucleotide may comprise a Unique Molecular Identifier (UMI) which differs for each oligonucleotide. The UMI may comprise 6 to 20 nucleotides in length. Each second oligonucleotide barcode may range from 4 to 100 nucleotides in length. The second oligonucleotide linker may be chemically-cleavable, enzymatically cleavable, or photocleavable. The second oligonucleotide linker may be different from the aptamer oligonucleotide linker, whereby the oligonucleotides may be cleaved by different mechanisms. The second oligonucleotide linker may be differentially cleavable as compared to the aptamer oligonucleotide linker, whereby each linker is capable of cleavage at different times. The copy number of oligonucleotides specific for different target proteins and second oligonucleotides on said solid support may be varied, whereby the solid support comprises a desired ratio of oligonucleotides for capturing proteins and mRNAs. The second oligonucleotides may comprise 1-5% of oligonucleotides on said solid support and the oligonucleotides specific for different target proteins may comprise 95-99% of oligonucleotides on said solid support.

In another aspect, the present invention provides for a method of identifying proteins expressed in single cells comprising: segregating single cells with a solid support as described herein by a method comprising merging one uniquely barcoded bead with a single-cell in an emulsion droplet, microfluidic drop, or microwell, or a method comprising adding a single cell to a microwell comprising a barcoded surface; lysing the cells and cleaving the linkers in a buffer that preserves aptamer-target recognition; incubating the lysed cells and oligonucleotides thereby capturing expressed aptamer target proteins on the cleaved oligonucleotides; pooling the samples after breaking droplets or pooling the samples from microwells; optionally, functionalizing proteins; isolating oligo-aptamer protein complexes; and preparing and sequencing a single composite sequencing library, whereby the cell barcodes record the cell-of-origin of each oligonucleotide sequence and target barcodes record expressed proteins from the same cell. Conditions for aptamer binding are well known in the art. The proteins may be functionalized with biotin. In certain embodiments, isolating oligo-aptamer protein complexes from oligo-aptamer molecules may comprise any method that is based on characteristics not shared with DNA as described herein. The isolating of oligo-aptamer protein complexes may comprise streptavidin bead purification. The isolating oligo-aptamer protein complexes may comprise conjugation of proteins to functionalized beads.

In another aspect, the present invention provides for a method of identifying proteins expressed in single cells comprising: segregating single cells with a solid support as described herein by a method comprising merging one uniquely barcoded bead with a single-cell in an emulsion droplet, microfluidic drop, or microwell, or a method comprising adding a single cell to a microwell comprising a barcoded surface, wherein the cells are lysed in a buffer that preserves highly specific aptamer-target recognition; incubating the lysed cells with the beads or surfaces thereby capturing expressed aptamer target proteins on each bead or surface; wherein beads are used, breaking droplets or isolating beads from microwells and pooling the beads in solution; washing the beads or surfaces, wherein unbound proteins are removed; cleaving the linkers; isolating oligo-aptamer protein complexes from oligo-aptamer molecules; and preparing and sequencing a single composite sequencing library, whereby the cell barcodes record the cell-of-origin of each oligonucleotide sequence and target barcodes record expressed proteins from the same cell.

The method may further comprise covalently linking the aptamers to captured proteins after washing the beads or surfaces. Not being bound by a theory, covalently linking the aptamer to the target protein prevents dissociating the interaction during downstream processing steps (e.g., isolating aptamer protein complexes). The step of covalently linking is preferably performed at any step following the incubating step and before isolating oligo-aptamer protein complexes. In a preferred embodiment, covalently linking the aptamer to captured proteins occurs after the washing step, thus unbound proteins are removed and non-specific protein-aptamer coupling is avoided. The method may further comprise functionalizing proteins after washing the beads or surfaces or after covalently linking the aptamers to captured proteins. The linkers may be cleaved enzymatically, chemically or by UV treatment and said functionalizing proteins may be performed before said cleavage. In the case where linkers are cleaved enzymatically, functionalizing is performed before cleavage to avoid functionalizing the enzyme and causing non-specific interactions. In other words, the order prevents the cleaving enzyme to contribute to the background signal (any protein that binds DNA would get biotinylated and get purified non-specifically otherwise). The linkers may be cleaved chemically or by UV treatment and said functionalizing proteins may be performed after said cleavage. Not being bound by a theory, cleavage by use of a chemical or by UV treatment does not require a protein that may become functionalized and thus functionalizing proteins can be performed before or after cleavage. The proteins may be functionalized with biotin. The isolating of oligo-aptamer protein complexes from oligo-aptamer molecules may comprise streptavidin bead purification. The isolating of oligo-aptamer protein complexes from oligo-aptamer molecules may comprise conjugation of proteins to functionalized beads as described herein.

In another aspect, the present invention provides for a method of identifying proteins and mRNAs expressed in single cells comprising: segregating single cells with a solid support as described herein comprising oligonucleotides for capturing proteins and oligonucleotides for capturing mRNA, wherein the first and second oligonucleotides comprises different cleavable linkers, wherein the cells are lysed in a buffer that preserves aptamer-target recognition; incubating the lysed cells thereby capturing expressed aptamer target proteins and mRNAs on the first and second oligonucleotides; separating the first oligonucleotides from the second oligonucleotides; performing a reverse transcription reaction on the second oligonucleotides, whereby cDNA is obtained; isolating oligo-aptamer protein complexes from the first oligonucleotides; and preparing and sequencing a single composite sequencing library for each of oligo-aptamer protein complexes and cDNA, wherein the second oligonucleotides are cleaved from the solid support before separating the first oligonucleotides from the second oligonucleotides, wherein the first oligonucleotides are cleaved after separating the first oligonucleotides from the second oligonucleotides and before isolating oligo-aptamer protein complexes from the first oligonucleotides. The segregating may comprise merging one uniquely barcoded bead with a single-cell in an emulsion droplet, microfluidic drop, or microwell, wherein after step incubating the lysed cells droplets are broken or beads are isolated from microwells and the beads are pooled in solution, optionally separating the first oligonucleotides from the second oligonucleotides comprises separating supernatants comprising cleaved second oligonucleotides, optionally the beads are washed before cleavage of the second and/or first oligonucleotides. The segregating may comprise adding a single cell to a microwell comprising a barcoded surface, wherein optionally separating the first oligonucleotides from the second oligonucleotides comprises separating supernatants comprising cleaved second oligonucleotides, optionally the surfaces are washed before cleavage of the second and/or first oligonucleotides.

In one embodiment, single cells are segregated with a solid support, the cells are lysed and the linkers attached to the oligonucleotides for capturing mRNA are cleaved, and the segregated cells are incubated. If the solid supports are beads in droplets, then droplets are broken leaving a pool of supernatants and beads. The supernatants contain the mRNA captured by oligonucleotides and the beads contain captured proteins. If the solid supports are beads in microwells, then the supernatants contain the mRNA captured by oligonucleotides and the beads contain captured proteins. If the solid supports are surfaces of microwells, then the supernatants contain the mRNA captured by oligonucleotides and the surfaces contain captured proteins. The supernatants can then be separated from the solid supports. The solid supports may then be washed. The oligonucleotides containing the captured proteins may then be cleaved and the protein-aptamer oligonucleotide complexes may be isolated. In the last step, separate sequencing libraries are constructed for mRNA and proteins and sequenced.

In another embodiment, single cells are segregated with a solid support, the cells are lysed, and the segregated cells are incubated. If the solid supports are beads in droplets, then droplets are broken and beads are pooled. If the solid supports are beads in microwells, then the beads are spun out of the wells. If the solid supports are surfaces of microwells, then the supernatants are removed from the surfaces. The solid supports may then be washed. The linkers attached to the oligonucleotides for capturing mRNA are then cleaved. The supernatant containing the cleaved oligonucleotides may then be separated from the solid supports. The solid supports may be washed again. The proteins may be functionalized after washing as described herein. The oligonucleotides containing the captured proteins may then be cleaved and the protein-aptamer oligonucleotide complexes may be isolated. In the last step, separate sequencing libraries are constructed for mRNA and proteins and sequenced.

The method may further comprise covalently linking the aptamers to captured proteins after washing the beads or surfaces. Not being bound by a theory, covalently linking the aptamer to the target protein prevents dissociating the interaction during downstream processing steps (e.g., isolating aptamer protein complexes). The step of covalently linking is preferably performed at any step following the incubating step and before isolating oligo-aptamer protein complexes. In a preferred embodiment, covalently linking the aptamer to captured proteins occurs after the washing step, thus unbound proteins are removed and non-specific protein-aptamer coupling is avoided. The method may further comprise functionalizing proteins after washing the beads or surfaces or after covalently linking the aptamers to captured proteins. The linkers may be cleaved enzymatically, chemically or by UV treatment and said functionalizing proteins may be performed before said cleavage. In the case where linkers are cleaved enzymatically, functionalizing is performed before cleavage to avoid functionalizing the enzyme and causing non-specific interactions. In other words, the order prevents the cleaving enzyme to contribute to the background signal (any protein that binds DNA would get biotinylated and get purified non-specifically otherwise). The linkers may be cleaved chemically or by UV treatment and said functionalizing proteins may be performed after said cleavage. Not being bound by a theory, cleavage by use of a chemical or by UV treatment does not require a protein that may become functionalized and thus functionalizing proteins can be performed before or after cleavage. The proteins may be functionalized with biotin. The isolating of oligo-aptamer protein complexes from oligo-aptamer molecules may comprise streptavidin bead purification. The isolating of oligo-aptamer protein complexes from oligo-aptamer molecules may comprise conjugation of proteins to functionalized beads as described herein.

In another aspect, the present invention provides for a method of identifying proteins and mRNAs expressed in single cells comprising: segregating single cells with a solid support as described herein comprising oligonucleotides for capturing proteins and oligonucleotides for capturing mRNA, wherein the first and second oligonucleotides comprises different cleavable linkers, by a method comprising merging one uniquely barcoded bead with a single-cell in an emulsion droplet, microfluidic drop, or microwell, or a method comprising adding a single cell to a microwell comprising a barcoded surface, wherein the cells are lysed in a buffer that preserves aptamer-target recognition; incubating the lysed cells thereby capturing expressed aptamer target proteins and mRNAs on the beads or surfaces; wherein beads are used, breaking droplets or isolating beads from microwells and pooling the beads in solution; washing the beads or surfaces, wherein unbound proteins are removed; cleaving the second oligonucleotide linkers; separating the supernatant comprising second oligonucleotides from the beads or surfaces; performing a reverse transcription reaction on the supernatant, whereby the mRNA is converted to first strand cDNA; cleaving the aptamer oligonucleotide linkers; isolating oligo-aptamer protein complexes; and preparing and sequencing a single composite sequencing library for each of oligo-aptamer protein complexes and cDNA.

In another aspect, the present invention provides for a method of identifying proteins and mRNAs expressed in single cells comprising: segregating single cells with a solid support as described herein comprising oligonucleotides for capturing mRNA and oligonucleotides for capturing proteins by a method comprising merging one uniquely barcoded bead with a single-cell in an emulsion droplet, microfluidic drop, or microwell, or a method comprising adding a single cell to a microwell comprising a barcoded surface, wherein the cells are lysed in a buffer that preserves aptamer-target recognition; incubating the lysed cells thereby capturing expressed aptamer target proteins and mRNAs on the beads or surfaces; wherein beads are used, breaking droplets or isolating beads from microwells and pooling the beads in solution; washing the beads or surfaces, wherein unbound proteins are removed; performing a reverse transcription reaction, whereby the mRNA is converted to first strand cDNA, optionally, performing a reverse transcription reaction comprising alkyne functionalized nucleotides, whereby the mRNA is converted to biotinylated first strand cDNA; cleaving the linkers; isolating oligo-aptamer protein complexes, and optionally cDNA by a method comprising streptavidin bead purification; and preparing and sequencing a single composite sequencing library, optionally preparing and sequencing a single composite sequencing library for each of oligo-aptamer protein complexes and cDNA.

The methods of identifying proteins and mRNAs expressed in single cells may further comprise covalently linking the aptamers to captured proteins after washing the beads or surfaces. Not being bound by a theory, covalently linking the aptamer to the target protein prevents dissociating the interaction during downstream processing steps (e.g., isolating aptamer protein complexes). The step of covalently linking is preferably performed at any step following the incubating step and before isolating oligo-aptamer protein complexes. In a preferred embodiment, covalently linking the aptamer to captured proteins occurs after the washing step, thus unbound proteins are removed and non-specific protein-aptamer coupling is avoided. The method may further comprise functionalizing proteins after washing the beads or surfaces or after covalently linking the aptamers to captured proteins. The linkers may be cleaved enzymatically, chemically or by UV treatment and said functionalizing proteins may be performed before said cleavage. In the case where linkers are cleaved enzymatically, functionalizing is performed before cleavage to avoid functionalizing the enzyme and causing non-specific interactions. In other words, the order prevents the cleaving enzyme to contribute to the background signal (any protein that binds DNA would get biotinylated and get purified non-specifically otherwise). The linkers may be cleaved chemically or by UV treatment and said functionalizing proteins may be performed after said cleavage. Not being bound by a theory, cleavage by use of a chemical or by UV treatment does not require a protein that may become functionalized and thus functionalizing proteins can be performed before or after cleavage. The proteins may be functionalized with biotin. The isolating of oligo-aptamer protein complexes from oligo-aptamer molecules may comprise streptavidin bead purification. The isolating of oligo-aptamer protein complexes from oligo-aptamer molecules may comprise conjugation of proteins to functionalized beads as described herein.

In another aspect, the present invention provides for a method of identifying proteins and mRNAs expressed in single cells comprising: segregating single cells with a solid support as described herein comprising oligonucleotides for capturing mRNA and oligonucleotides for capturing proteins by a method comprising merging one uniquely barcoded bead with a single-cell in an emulsion droplet, microfluidic drop, or microwell, or a method comprising adding a single cell to a microwell comprising a barcoded surface; lysing the cells and cleaving the linkers in a buffer that preserves aptamer-target recognition; incubating the lysed cells thereby capturing expressed aptamer target proteins and mRNAs on the cleaved oligonucleotides; pooling the samples after breaking droplets or pooling the samples from microwells; optionally, functionalizing proteins; isolating oligo-aptamer complexes; performing a reverse transcription reaction, whereby the mRNA is converted to first strand cDNA; and preparing and sequencing a single composite sequencing library for each of oligo-aptamer protein complexes and cDNA. The proteins may be functionalized with biotin. In certain embodiments, isolating oligo-aptamer protein complexes from oligo-aptamer molecules may comprise any method that is based on characteristics not shared with DNA as described herein. The isolating of oligo-aptamer protein complexes may comprise streptavidin bead purification. The isolating oligo-aptamer protein complexes may comprise conjugation of proteins to functionalized beads.

In another aspect, the present invention provides for a method of identifying proteins expressed in single cells that are in proximity comprising: segregating single cells with a single solid support as described herein comprising oligonucleotides comprising an aptamer and a universal hybridization sequence by a method comprising merging one uniquely barcoded bead with a single-cell in an emulsion droplet, microfluidic drop, or microwell or a method comprising adding a single cell to a microwell comprising a barcoded surface, wherein the cells are lysed in a buffer that preserves aptamer-target recognition; incubating the lysed cells thereby capturing expressed aptamer target proteins on the beads or surfaces; wherein beads are used, breaking droplets or isolating beads from microwells and pooling the beads in solution; washing the beads or surfaces, wherein unbound proteins are removed; incubating the captured oligo-aptamer protein complexes with a set of second oligonucleotide linked affinity reagents comprising i) an aptamer, antibody or antibody fragment, ii) a sequencing primer sequence, iii) a target barcode and iv) a 6 to 12 nucleotide hybridization sequence, wherein when a second affinity reagent binds to an interacting protein the hybridization sequence binds to the universal hybridization sequence; washing the beads or surfaces, wherein unbound second affinity reagents are removed; performing DNA polymerase extension using the dsDNA hybridization region as a primer, whereby a DNA strand is synthesized comprising the barcodes corresponding to both proteins; and preparing and sequencing a single composite sequencing library, whereby the cell barcodes record the cell-of-origin of each oligonucleotide sequence and target barcodes record the proteins in proximity. In certain embodiments, the proteins in proximity are interacting proteins. Not being bound by a theory, only oligonucleotides that record an interacting protein or proteins in proximity contains the reverse PCR primer. The extended oligonucleotide is the strand opposite the strand linked to the first aptamer. In certain embodiments, the extended strand is hybridized to the strand linked to the bead. In certain embodiments, the linkers are cleaved to release the oligonucleotides. Not being bound by a theory, the library can be specifically amplified without isolating aptamer-oligonucleotide protein complexes to detect a protein-protein interaction because only oligonucleotides that record an interacting protein contains the reverse PCR primer. In certain embodiments, aptamer-oligonucleotide protein complexes are isolated. In certain embodiments, the second set of oligonucleotide linked affinity reagents may be any affinity ligand comprising a sequencing primer sequence, a target barcode and a 6 to 12 nucleotide hybridization sequence.

In another aspect, the present invention provides for a method of identifying post translationally modified proteins expressed in single cells comprising: segregating single cells with a single solid support as described herein comprising oligonucleotides comprising an aptamer and a universal hybridization sequence by a method comprising merging one uniquely barcoded bead with a single-cell in an emulsion droplet, microfluidic drop, or microwell or a method comprising adding a single cell to a microwell comprising a barcoded surface, wherein the cells are lysed in a buffer that preserves aptamer-target recognition; incubating the lysed cells thereby capturing expressed aptamer target proteins on the beads or surfaces; wherein beads are used, breaking droplets or isolating beads from microwells and pooling the beads in solution; washing the beads or surfaces, wherein unbound proteins are removed; incubating the captured oligo-aptamer protein complexes with a set of second oligonucleotide linked affinity reagents specific for target post translational modifications comprising i) an aptamer, antibody or antibody fragment, ii) a sequencing primer sequence, iii) a target barcode and iv) a 6 to 12 nucleotide hybridization sequence, wherein when an affinity reagent binds to a post translational modification on a captured protein the hybridization sequence binds to the universal hybridization sequence; washing the beads or surfaces, wherein unbound affinity reagents are removed; performing DNA polymerase extension using the dsDNA hybridization region as a primer, whereby a DNA strand is synthesized comprising the barcodes corresponding to both target protein and target post translational modification; and preparing and sequencing a single composite sequencing library, whereby the cell barcodes record the cell-of-origin of each oligonucleotide sequence and target barcodes record the target protein and target post translational modification. In certain embodiments, the second set of oligonucleotide linked affinity reagents may be any affinity ligand comprising a sequencing primer sequence, a target barcode and a 6 to 12 nucleotide hybridization sequence.

In another aspect, the present invention provides for a method of identifying proteins and mRNAs expressed in single cells comprising: segregating single cells with a single solid support as described herein comprising oligonucleotides comprising an aptamer and a poly T sequence by a method comprising merging one uniquely barcoded bead with a single-cell in an emulsion droplet, microfluidic drop, or microwell or a method comprising adding a single cell to a microwell comprising a barcoded surface; lysing the cells and cleaving the linkers in a buffer that preserves aptamer-target recognition; incubating the lysed cells and oligonucleotides thereby capturing expressed aptamer target proteins and mRNAs on the cleaved oligonucleotides; wherein beads are used, pooling the samples after breaking droplets or pooling the samples from microwells; optionally, functionalizing proteins; isolating oligo-aptamer protein complexes from oligo-aptamer molecules; performing reverse transcription extension using the poly T hybridization region as a primer, whereby a DNA strand is synthesized containing a barcode corresponding to a captured protein and a mRNA; and preparing and sequencing a single composite sequencing library. Not being bound by a theory, the poly T sequence can capture any mRNA and not just mRNA bound to protein complexes. However, mRNA transcripts that tend to bind to the aptamer target would be enriched compared to non-interacting mRNA transcripts, and isolating protein oligonucleotide complexes allows enrichment of target protein-mRNA transcript pairs. In certain embodiments, isolating oligo-aptamer protein complexes from oligo-aptamer molecules may comprise any method that is based on characteristics not shared with DNA as described herein. The proteins may be functionalized with biotin. The isolating of oligo-aptamer protein complexes may comprise streptavidin bead purification. The isolating oligo-aptamer protein complexes may comprise conjugation of proteins to functionalized beads.

In another aspect, the present invention provides for a method of identifying proteins and mRNAs expressed in single cells comprising: segregating single cells with a single solid support as described herein comprising oligonucleotides comprising an aptamer and a poly T sequence a method comprising merging one uniquely barcoded bead with a single-cell in an emulsion droplet, microfluidic drop, or microwell or a method comprising adding a single cell to a microwell comprising a barcoded surface, wherein the cells are lysed in a buffer that preserves aptamer-target recognition; incubating the lysed cells thereby capturing expressed aptamer target proteins and mRNAs on each bead or surface; wherein beads are used, breaking droplets or isolating beads from microwells and pooling the beads in solution; washing the beads or surfaces, wherein unbound proteins are removed; cleaving the linkers; isolating oligo-aptamer protein complexes from oligo-aptamer molecules; performing reverse transcription extension using the poly T hybridization region as a primer, whereby a DNA strand is synthesized containing a barcode corresponding to a captured protein and a mRNA; and preparing and sequencing a single composite sequencing library. Not being bound by a theory, the poly T sequence can capture any mRNA and not just mRNA bound to protein complexes. Therefore, isolating protein oligonucleotide complexes allows enrichment of target protein-mRNA transcript pairs.

The method may further comprise covalently linking the aptamers to captured proteins after washing the beads or surfaces. Not being bound by a theory, covalently linking the aptamer to the target protein prevents dissociating the interaction during downstream processing steps (e.g., isolating aptamer protein complexes). The step of covalently linking is preferably performed at any step following the incubating step and before isolating oligo-aptamer protein complexes. In a preferred embodiment, covalently linking the aptamer to captured proteins occurs after the washing step, thus unbound proteins are removed and non-specific protein-aptamer coupling is avoided. The method may further comprise functionalizing proteins after washing the beads or surfaces or after covalently linking the aptamers to captured proteins. The linkers may be cleaved enzymatically, chemically or by UV treatment and said functionalizing proteins may be performed before said cleavage. In the case where linkers are cleaved enzymatically, functionalizing is performed before cleavage to avoid functionalizing the enzyme and causing non-specific interactions. In other words, the order prevents the cleaving enzyme to contribute to the background signal (any protein that binds DNA would get biotinylated and get purified non-specifically otherwise). The linkers may be cleaved chemically or by UV treatment and said functionalizing proteins may be performed after said cleavage. Not being bound by a theory, cleavage by use of a chemical or by UV treatment does not require a protein that may become functionalized and thus functionalizing proteins can be performed before or after cleavage. The proteins may be functionalized with biotin. The isolating of oligo-aptamer protein complexes from oligo-aptamer molecules may comprise streptavidin bead purification. The isolating of oligo-aptamer protein complexes from oligo-aptamer molecules may comprise conjugation of proteins to functionalized beads as described herein.

In certain embodiments, any method known in the art for incubation as performed during protein purification or immunoprecipitation may be used. In certain embodiments, any method as described herein may comprise an incubation step performed between 4 to 37° C. In certain embodiments, isolating oligo-aptamer protein complexes from oligo-aptamer molecules may comprise any method that is based on characteristics not shared with DNA (e.g., linking to amines, thiols, on the proteins). Click chemistry reactions may also be used to specifically isolate protein containing complexes (see, e.g., Kolb, H. C., Finn, M. G. and Sharpless, K. B. (2001), Click Chemistry: Diverse Chemical Function from a Few Good Reactions. Angewandte Chemie International Edition, 40: 2004-2021; and Hoyle, Charles E. and Bowman, Christopher N. (2010), Thiol-Ene Click Chemistry. Angewandte Chemie International Edition, 49: 1540-1573). In certain embodiments, isolating oligo-aptamer protein complexes from oligo-aptamer molecules may comprise biotinylation of proteins and streptavidin bead purification. In certain embodiments, isolating oligo-aptamer protein complexes from oligo-aptamer molecules may comprise conjugation of primary amine groups on the proteins to carboxylated functionalized beads.

In another aspect, the present invention provides for a method of preparing oligonucleotide-adorned solid supports for identifying proteins expressed in single cells comprising: preparing solid supports linked to a plurality of oligonucleotides, each oligonucleotide comprising a linker directly attached to a solid support, a sequencing priming site, a cell barcode, and a hybridization sequence, optionally, a UMI; and adding to said solid supports a plurality of aptamer oligonucleotides, each aptamer oligonucleotide comprising a sequence complementary to the hybridization sequence, a target barcode specific for an aptamer, and an aptamer; and extending the oligonucleotides linked to the solid supports, wherein the aptamer oligonucleotides comprising individual aptamers are pooled before adding to said solid supports, such that a desired ratio of individual aptamers is obtained on said solid supports. The method may further comprise a spacer between the aptamer and the oligonucleotide strand, wherein the spacer functions as a blocking agent against DNA polymerase extension.

In another aspect, the present invention provides for a method of preparing oligonucleotide-adorned solid supports for identifying proteins expressed in single cells comprising: preparing solid supports linked to a plurality of oligonucleotides, each oligonucleotide comprising a linker directly attached to a solid support, a sequencing priming site, a cell barcode, and a ligation sequence, optionally, a UMI; and adding to said solid supports for ligation, a plurality of aptamer oligonucleotides, each aptamer oligonucleotide comprising a hybridization sequence specific for the ligation sequence, a target barcode specific for an aptamer, and the aptamer; and ligating the oligonucleotides attached to the solid supports to the aptamer oligonucleotides, wherein the aptamer oligonucleotides comprising individual aptamers are pooled before adding to said solid supports for ligation, such that a desired ratio of individual aptamers is obtained on said solid support.

In one embodiment, the method of preparing oligonucleotide-adorned solid supports for identifying proteins expressed in single cells may comprise preparing a cell barcode by at least two cycles of split and pool synthesis on the solid support. The oligonucleotides may further comprise a reverse priming site after the target barcode sequence, whereby by the cell and target barcodes may be amplified by PCR. The solid support may be a bead. The bead may be a magnetic bead. The bead may be a deformable bead. The bead may be a hydrogel bead. The solid support may be a surface of a microwell. The surface may comprise a hydrogel surface. In certain embodiments, the surface of a microwell is coated by any know process such that oligonucleotides may be linked, e.g., a hydrogel.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A-H illustrates aptamer oligonucleotide synthesis. FIG. 1A shows the common DNA primer: photo-cleavable spacer and sequencing primer NXT1. FIG. 1B and FIG. 1C shows the oligonucleotide comprising a NXT hybridization sequence, cellular barcode 1, and hybridization 1 sequence is hybridized to the common primer and is extended.

FIG. 1D, FIG. 1E and FIG. 1F shows the oligonucleotide with a complementary hybridization 1 sequence, cellular barcode 2, and hybridization 2 sequence is hybridized to the prior primer and is extended in both directions. FIG. 1G and FIG. 1H show a custom synthesized aptamer oligonucleotide with a complementary hybridization 2 sequence, protein barcode, UMI, sequencing primer NXT2, spacer, and the aptamer oligonucleotide is hybridized to the prior primer and is extended in both directions. Extension is stopped by the spacer.

FIG. 2A shows the common DNA primer: photo-cleavable spacer and sequencing primer NXT1. FIG. 2B and FIG. 2C shows the oligonucleotide comprising a NXT hybridization sequence, cellular barcode 1, and hybridization 1 sequence is hybridized to the common primer and is extended. FIG. 2D, FIG. 2E and FIG. 2F shows the oligonucleotide with a complementary hybridization 1 sequence, cellular barcode 2, and hybridization 2 sequence is hybridized to the prior primer and is extended in both directions. FIG. 2G and FIG. 2H show a custom synthesized aptamer oligonucleotide comprising a complementary hybridization 2 sequence, protein barcode, UMI, sequencing primer NXT2, spacer, and aptamer is hybridized to a complementary oligonucleotide sequence, wherein the hybridization 2 sequence remains ssDNA and the sequence includes a hybridization 3 sequence. FIG. 2I shows a target protein binds to aptamer 1. The oligonucleotide aptamer complexes are then incubated with second aptamer oligonucleotides comprising a complementary hybridization 3 sequence, protein 2 barcode, sequencing primer NXT3, spacer and aptamer 2. Upon binding of the second aptamer oligonucleotide to a protein-protein complex, the hybridization 3 sequences may hybridize. Extension using the hybridization 3 sequence as a primer results in a sequence including the three barcodes and sequencing primer sites.

DETAILED DESCRIPTION OF THE EXAMPLE EMBODIMENTS

General Definitions

Figure 2A:
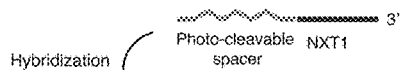
FIG. 2A-I illustrates an oligonucleotide for detecting protein interactions.
Figure 2B:
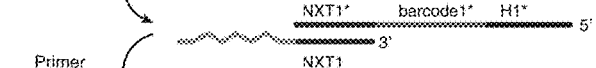
Figure 2C:
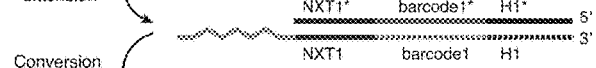
Figure 2D:
Figure 2E:
Figure 2F:
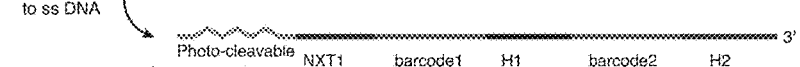
Figure 2G:
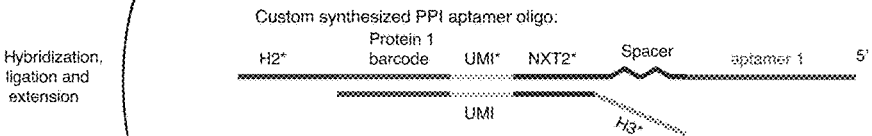
Figure 2H:
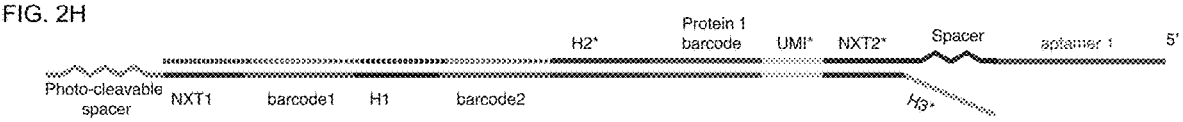
Figure 2I:
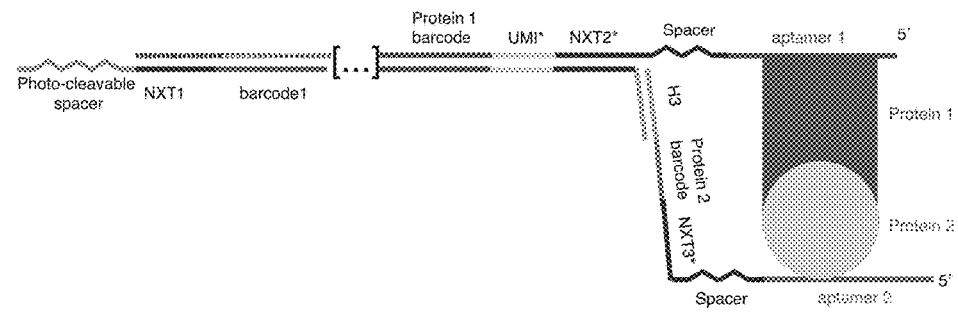

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +1-10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to International Patent numbers PCT/US16/059233, filed Oct. 27, 2016, PCT/US2016/059195, filed Oct. 27, 2016, and PCT/US16/059230 filed Oct. 27, 2016.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods and apparatuses for single-cell proteomic analysis. In certain embodiments, the methods leverage the use of protein specific aptamers, microfluidics, and barcoding to provide a sequencing based readout for quantifying protein expression in single cells. Additional embodiments provide for coupling proteomic and gene expression analysis in single cells. Additional embodiments also provide for detecting protein interactions in single cells.

Aptamers

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro 2'-F), and/or 2'-0-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example; one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res, 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colo.). In certain embodiments, the present invention may utilize any aptamer containing any modification as described herein.

As used herein, the term "preserving aptamer-target recognition" refers to preserving the native conformation of the target proteins and conditions that allow aptamer binding to target proteins.

Antibodies

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

Antibodies may be specific for any target protein or target protein modification. Any protein modification, especially post-translational protein modification, can be assessed by the present method. Exemplary protein modifications that can be assessed by the present method include phosphorylation, acetylation, methylation, ADP-ribosylation, addition of a polypeptide side chain, addition of a hydrophobic group, and addition of a carbohydrate. In one specific embodiment, the phosphorylation to be assessed is phosphorylation on tyrosine, serine, threonine or histidine residue. In another specific embodiment, acetylation to be assessed is acetylation on lysine. In another specific embodiment, methylation to be assessed is methylation on lysine or arginine. In another specific embodiment, the addition of a polypeptide side chain to be assessed is the addition of ubiquitin. In still another specific embodiment, the addition of a hydrophobic group to be assessed is the addition of a fatty acid, e.g., myristate or palmitate, addition of an isoprenoid, e.g., farnesyl or genranylgenranyl, or addition of a glycosyl-phosphatidyl inositol anchor, e.g., a carbohydrate group comprises glycosyl. Probes specific for cholesterol may be used (see, e.g., Gimpl, Cholesterol-Protein Interaction: Methods and Cholesterol Reporter Molecules, Cholesterol Binding and Cholesterol Transport Proteins: Volume 51 of the series Subcellular Biochemistry pp 1-45; and Gimpl and Gehrig-Burger, Probes for studying cholesterol binding and cell biology, Steroids. 2011 February; 76(3):216-31). The present invention may be used with any probe that can be functionalized with an oligonucleotide as described herein.

Methods for attaching nucleic acids to antibodies are well known in the art, and any suitable approach is encompassed within the presently disclosed methods, compositions, and kits (see, e.g., WO2016100976 A2). For example, in some embodiments antibodies may be attached to nucleic acid molecules using the methods described in Gullberg, et al. (2004), PNAS 101(22):8420-8424, and Boozer, et al. (2004), Analytical Chemistry 76(23):6967-6972, both of which are incorporated herein by reference. In some embodiments, antibodies may be attached to nucleic acid molecules by random coupling to free amines. In some embodiments, the antibodies may be attached to nucleic acid molecules by random coupling to free amines using a 10-to-1 ratio of nucleic acid to antibody. In some embodiments, antibodies may be attached to nucleic acid molecules using the methods described in Kozlov, et al. (2004), Biopolymers, 73 621-630, which is incorporated herein by reference. In some embodiments, antibodies may be attached to nucleic acid molecules using hydrazine chemistry. In some embodiments, antibodies may be attached to nucleic acid molecules using "tadpoles" as described in Nolan (2005), Nature Methods 2: 11-12, which is incorporated herein by reference. In general, antibodies may be attached to nucleic acid molecules using any suitable method known in the art for generating engineered antibodies, including the methods described herein.

Nucleic Acid Barcode, Barcode, and Unique Molecular Identifier (UMI)

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The target nucleic acid to be sequenced may be an aptamer oligonucleotide as described herein and the UMI may be used to indicate the number of target molecules captured. Each oligonucleotide may capture a single target protein and each oligonucleotide comprises a different UMI. The UMI may also be used to determine the number of transcripts that gave rise to an amplified product, or in the case of target barcodes as described herein, the number of binding events. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No:11, 163-166). Not being bound by a theory, the UMI's are designed such that assignment to the original can take place despite up to 4-7 errors during amplification or sequencing. Not being bound by a theory, an UMI may be used to discriminate between true barcode sequences.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type NNNNNNNNNNNN.

A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semi-solid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. Methods for constructing sequencing libraries are known in the art (see, e.g., Head et al., Library construction for next-generation sequencing: Overviews and challenges. Biotechniques. 2014; 56(2): 61-77).

In certain embodiments, highly conserved sequences present a technical limitation on some sequencing platforms that utilize fluorescent detection (i.e., Illumina). This can occur with amplicon-based sequencing such as microbiome studies using 16S rRNA for species identification. In certain embodiments, the oligonucleotides of the present invention include highly conserved sequences. For example, conserved hybridization sequences may be used to generate a barcode comprising two indices, whereby the indices are separated by a conserved hybridization sequence. In this situation, the conserved sequences at the beginning of the read will generate the exact same base with each cycle of sequencing, creating problems for the signal detection hardware and software. This limitation is not an issue with Ion Torrent systems (not fluorescence-based) and can be addressed on Illumina systems by sequencing multiple different amplicons in the same lane whenever possible. An alternative strategy is to use several PCR primers during PCR of a specific amplicon. Each primer has a different number of bases (typically 1-3 random bases) added to the 5' end to offset/stagger the order of sequencing when adapters are ligated to the amplicons. In one embodiment and as described further herein, the first index may include an additional 1 to 3 random bases to stagger the sequencing of the conserved sequence.

In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

Barcodes Reversibly Coupled to Solid Substrate

In some embodiments, the origin-specific barcodes are reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

Barcode with Cleavage Sites

A nucleic acid barcode may be cleavable from a specific binding agent, for example, after the specific binding agent has bound to a target molecule. In some embodiments, the origin-specific barcode further comprises one or more cleavage sites. In some examples, at least one cleavage site is oriented such that cleavage at that site releases the origin-specific barcode from a substrate, such as a bead, for example a hydrogel bead, to which it is coupled. In some examples, at least one cleavage site is oriented such that the cleavage at the site releases the origin-specific barcode from the target molecule specific binding agent. In some examples, a cleavage site is an enzymatic cleavage site, such a endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage.

Barcode Adapters

In some embodiments, the target molecule is attached to an origin-specific barcode receiving adapter, such as a nucleic acid. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Barcode with Capture Moiety

In some embodiments, an origin-specific barcode further includes a capture moiety, covalently or non-covalently linked. Thus, in some embodiments the origin-specific barcode, and anything bound or attached thereto, that include a capture moiety are captured with a specific binding agent that specifically binds the capture moiety. In some embodiments, the capture moiety is adsorbed or otherwise captured on a surface. In specific embodiments, a targeting probe is labeled with biotin, for instance by incorporation of biotin-16-UTP during in vitro transcription, allowing later capture by streptavidin. Other means for labeling, capturing, and detecting an origin-specific barcode include: incorporation of aminoallyl-labeled nucleotides, incorporation of sulfhydryl-labeled nucleotides, incorporation of allyl- or azide-containing nucleotides, and many other methods described in Bioconjugate Techniques ($2^{nd}$ Ed), Greg T. Hermanson, Elsevier (2008), which is specifically incorporated herein by reference. In some embodiments, the targeting probes are covalently coupled to a solid support or other capture device prior to contacting the sample, using methods such as incorporation of aminoallyl-labeled nucleotides followed by 1-Ethyl-3-(3-dimethylaminopropyl)carbodiimide (EDC) coupling to a carboxy-activated solid support, or other methods described in Bioconjugate Techniques. In some embodiments, the specific binding agent has been immobilized for example on a solid support, thereby isolating the origin-specific barcode.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a *crocus*?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequenceable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

In certain embodiments, the nucleic acid of the present invention may be amplified to generate a sequencing library. Any suitable amplification technique may be used, for instance, PCR, assembly PCR, polymerase cycling assembly, reverse transcriptase (RT) PCR amplification, in vitro transcription amplification (IVT), multiple displacement amplification (MDA), or quantitative real-time PCR (qPCR), or the like. The target sequence or template may be amplified within droplets (see, e.g., U.S. Pat. Apl. Pub. No. 2010/0136544, 2014/0199730, or 2014/0199731), or in bulk solution. Multiple displacement amplification (MDA), is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

The oligonucleotides according to the present invention may also contain a variety of sequences. For example, the oligonucleotide may contain one or more primer sequences, one or more unique or "barcode" sequences as discussed herein, one or more promoter sequences, one or more spacer sequences, or the like. The oligonucleotide may also contain, in some embodiments one or more cleavable spacers, e.g., photocleavable linker. The oligonucleotide may in some embodiments be attached to a particle chemically (e.g., via a linker) or physically (e.g., without necessarily requiring a linker), e.g., such that the oligonucleotides can be removed from the particle via cleavage. Other examples include portions that may be used to increase the bulk (or length) of the oligonucleotides (e.g., using specific sequences or non-sense sequences), to facilitate handling (for example, an oligonucleotide may include a poly-A tail), to increase selectivity of binding (e.g., as discussed below), to facilitate recognition by an enzyme (e.g., a suitable ligase), to facilitate identification, or the like.

Microfluidics and Droplet Sequencing

The present invention provides for cell-of-origin barcodes introduced by oligonucleotide adorned solid supports to distinguish target proteins and optionally, mRNA, between single cells. The target proteins are distinguished by aptamer specific target barcodes. In certain embodiments, in order for single cells to receive a unique cell barcode, a single cell and single solid support of the present invention may be sorted into individual wells of a multi-well plate, microfluidic reaction chambers, such as by using the Fluidigm C1 system, or preferably, single droplets.

In one embodiment, single cells are sorted into separate wells by dilution of the cells and/or physical movement, such as by pipetting. Cells may also be sorted by any cell sorter known in the art, such as, but not limited to FACS. Each well may include a single barcoded bead or barcoded surface of the present invention. A machine may control the pipetting and sorting. The machine may be computer controlled. The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. In certain preferred embodiments, multi-well plates are used with magnetic beads of the present invention. Not being bound by a theory, the use of magnetic beads in conjunction with a magnetic source facilitates washing of the beads in a plate.

In a preferred embodiment, single cell analysis is performed using microfluidics. Microfluidics involves microscale devices that handle small volumes of fluids. Microfluidic reactions are generally conducted in microdroplets. The ability to conduct reactions in microdroplets depends on being able to merge different sample fluids and different microdroplets. See, e.g., US Patent Publication No. 20120219947, U.S. Pat. No. 9,364,803 and International Patent publication No. WO 2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. The use of microfluidics technology reduces cycle times, shortens time-to-results, and increases throughput. Furthermore, incorporation of microfluidics technology enhances system integration and automation. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment, single cell analysis is performed in droplets using methods according to WO 2014085802. Each of these patents and publications is herein incorporated by reference in their entireties for all purposes.

In preferred embodiments, single cells of the present invention are divided into single droplets using a microfluidic device. The single cells in such droplets may be incubated with the barcoded beads of the present invention, thus allowing a cell-of-origin to be recorded. Microfluidic devices useful for the present invention have been previously described and exemplary devices are further described in the below references. The beads may include beads known in the art and these beads are compatible with the oligonucleotides of the present invention. Moreover, methods of generating unique barcode sequences by a split and pool method are known in the art. In regard to microfluidic devices, barcodes, and beads, reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; and Gierahn et al., "Seq-Well: portable, low-cost RNA sequencing of single cells at high throughput" Nature Methods 14, 395-398 (2017) all the contents and disclosure of each of which are herein incorporated by reference in their entirety. Regarding split and pool generation of barcodes reference is also made to Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017, the contents and disclosure of each of which are herein incorporated by reference in their entirety. In preferred embodiments, the hydrogel beads, photocleavable spacers, barcoding method, and oligonucleotide release method are as described in Klein et al., 2015 and Zilionis, et al., 2017.

Although cells are used in this example as a source of nucleic acid material and proteins, this is by way of example, and in other embodiments, the nucleic acids and proteins may be introduced into the droplets from other sources, or using other techniques (e.g., nuclei, organelles, viruses). In certain embodiments, the invention involves protein detection in single nuclei. Not being bound by a theory, single nuclei may be isolated and contacted with the solid supports of the present invention in separate reaction volumes. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

Drop-seq methods and apparatus provides a high-throughput single-cell RNA-Seq and/or targeted nucleic acid profiling (for example, sequencing, quantitative reverse transcription polymerase chain reaction, and the like) where the RNAs or targeted nucleic acids from different cells are tagged individually, allowing a single library to be created while retaining the cell identity of each read. The present invention adapts the methods to provide high-throughput single-cell proteomics analysis using the beads of the present invention. The present invention allows for proteomics analysis, as well as concurrent analysis of RNA or targeted nucleic acid profile with proteomics analysis. Not being bound by a theory, the detection of both require the formation of droplets with a single bead, lysing of the cell, and capture of nucleic acids and/or proteins. Not being bound by a theory the conditions for lysing the cell is compatible for capture of both types of molecules. Thus, a combination of molecular barcoding and emulsion-based microfluidics to isolate, lyse, barcode, and prepare nucleic acids from individual cells in a high-throughput manner is used.

Microfluidic devices (for example, fabricated in polydimethylsiloxane), generate sub-nanoliter reverse emulsion droplets. These droplets are used to co-encapsulate proteins and/or nucleic acids with a barcoded capture bead. Each bead, for example, is uniquely barcoded so that each drop and its contents are distinguishable. The proteins and/or nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for preparing uniquely barcoded mRNA capture microbeads, which has a unique cell barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique cell barcodes on the surface of each bead in the pool (See www.ncbi.nlm.nih.gov/pmc/articles/PMC206447). In certain embodiments, oligonucleotides comprising an aptamer sequence and target barcode sequence are synthesized separately, by methods known in the art. Each aptamer sequence includes a target barcode sequence specific for the aptamer. The aptamer sequences can be conjugated to the cell barcode sequence, whereby beads are generated having a unique cell barcode sequence and the barcoded aptamer oligonucleotides.

Generally, the invention provides a method for preparing a large number of beads, particles, microbeads, nanoparticles, or the like with unique nucleic acid cell barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorically large number of distinct nucleic acid cell barcodes. The present invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Applicants present a complexed bead and a novel process for producing these beads where nucleotides are chemically built onto the bead material in a high-throughput manner followed by enzymatically attaching aptamer oligonucleotides as described herein. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: an oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide cell barcodes created by the described methods; additional oligonucleotide barcode sequences which vary among the oligonucleotides on an individual bead and can therefore be used to differentiate or help identify those individual oligonucleotide molecules (UMI); additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), aptamer sequences for capturing target proteins, or random sequences (for priming throughout the transcriptome or genome). In an embodiment, the individual oligonucleotide molecules on the surface of any individual microbead contain all three of these elements, and the third element includes an aptamer oligonucleotide sequence or oligo-dT. The microbeads preferably comprise a primer sequence for downstream sequencing of the barcodes associated with each bead.

In one embodiment, the single cells are poisson loaded into microwells (Fan et al., 2015). The aqueous droplets or microwells may be simultaneously loaded with barcoded beads, each of which has oligonucleotides including; a "cell barcode" that is the same across all the primers on the surface of any one bead, but different from the cell barcodes on all other beads; a Unique Molecular Identifier (UMI), different on each primer, that enables sequence reads derived from the same original DNA tag (amplification and PCR duplicates) to be identified computationally (Kivioja et al., 2012); and a capture sequence to bind the target proteins and/or oligonucleotides (either amplified PCR products or original DNA tags released by proteinase K treatment, or enzymatic/photonic oligo cleavage). Once the beads are loaded, they can be pooled for amplification and library preparation, and sequencing.

The beads according to the present invention can take multiple forms. Drop-seq beads are polystyrene, oligo functionalized beads, but alternative beads are possible, such as soft beads (polymer gel based beads, e.g., see www.10× genomics.com/technology), that allow for one on one pairing with cells, as to avoid the poisson loading needed in the drop-seq scheme. This reduces the amount of cells one needs, and makes it possible to analyze rare cell types or clinical samples only available in low amounts of cells. Beads or microspheres may refer to a hydrogel particle (polyacrylamide, agarose, etc.), or a colloidal particle (polystyrene, magnetic or polymer particle, etc.) of 1 to 500 micrometer in size, or other dimensions such as those described herein. The microspheres may be porous in some embodiments.

In some embodiments, the oligonucleotides are introduced into the droplets by initially attaching the oligonucleotides to a particle (e.g., a hydrogel or a polymeric particle), then subsequently releasing the oligonucleotides from the particle after the particle has been incorporated into a droplet. See, e.g., U.S. Pat. Apl. Ser. No. 62/072,944, filed Oct. 30, 2014 or PCT Apl. Ser. No. PCT/US2015/026443, filed on Apr. 17, 2015, entitled "Systems and Methods for Barcoding Nucleic Acids," each incorporated herein by reference. For example, in certain embodiments, the oligonucleotides may also contain a cleavable sequence or linker, or otherwise be releasable from the particles. In certain embodiments, the oligonucleotide may contain one or more cleavable linkers, e.g., that can be cleaved upon application of a suitable stimulus. For example, the cleavable sequence may be a photocleavable linker that can be cleaved by applying light or a cleavable linker that can be cleaved by applying a suitable chemical or enzyme.

The particles may be prepared in some cases such that most or all of the particles have a uniquely distinguishable oligonucleotide, relative to other particles having other distinguishable oligonucleotides. If the particles are present within the droplets at a density of 1 particle/droplet (or less), then once the oligonucleotides are released from the particle, then most or all of the droplets will contain one unique oligonucleotide (or no unique oligonucleotide), thus allowing each droplet (and the nucleic acids contained therein) to be uniquely identified.

In some embodiments, the particles may be encapsulated in droplets, such as microfluidic droplets. Those of ordinary skill in the art will be aware of techniques for encapsulating particles within microfluidic droplets; see, for example, U.S. Pat. Nos. 7,708,949, 8,337,778, 8,765,485, or Int. Pat. Apl. Pub. Nos. WO 2004/091763 and WO 2006/096571, each incorporated herein by reference. In some cases, the particles may be encapsulated at a density of less than 1 particle/droplet (and in some cases, much less than 1 particle/droplet) to ensure that most or all of the droplets have only zero or one particle present in them.

In certain embodiments, the solid support may also comprise a protective or passivating layer that can reduce or minimize non-specific attachment of components (e.g., proteins, nucleic acid molecules) to the binding surface during the assay which may lead to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein;

surfactants, e.g. zwitterionic surfactants, such as sulfobetaines; naturally occurring long-chain lipids; and nucleic acids, such as salmon sperm DNA.

In certain embodiments, any method known in the art for incubation as performed during protein purification or immunoprecipitation may be used in the present invention. In certain embodiments, any method as described herein may comprise an incubation step performed between 4 to 37° C. Applicants obtained capture of proteins on oligo-aptamer sequences at 37° C. In certain embodiments, isolating oligo-aptamer protein complexes from oligo-aptamer molecules may comprise any method that is based on characteristics not shared with DNA (e.g., linking to amines, thiols, on the proteins). Click chemistry reactions may also be used to specifically isolate protein containing complexes (see, e.g., Kolb, H. C., Finn, M. G. and Sharpless, K. B. (2001), Click Chemistry: Diverse Chemical Function from a Few Good Reactions. Angewandte Chemie International Edition, 40: 2004-2021; and Hoyle, Charles E. and Bowman, Christopher N. (2010), Thiol-Ene Click Chemistry. Angewandte Chemie International Edition, 49: 1540-1573). In certain embodiments, isolating oligo-aptamer protein complexes from oligo-aptamer molecules may comprise biotinylation of proteins and streptavidin bead purification. In certain embodiments, isolating oligo-aptamer protein complexes from oligo-aptamer molecules may comprise conjugation of primary amine groups on the proteins to carboxylated functionalized beads.

Perturb-Seq

Applicants have previously developed methods and tools for genome-scale screening of perturbations in single cells using CRISPR-Cas9, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). The present invention is compatible with perturb-seq, such that signature genes may be perturbed and the perturbation may be identified and assigned to the proteomic and gene expression readouts of single cells. In other words, genes or non-coding regulatory genomic loci may be perturbed in a population of cells and single cells may be analyzed by the methods of the present invention. The perturbations are preferably detected by detection of a barcoded transcript as described herein captured by an oligonucleotide configured for capturing mRNA.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed as described herein. In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence and reduces the chance of false guide RNA assignment. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed in is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, and single-cell analysis, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimising deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

The cell(s) may comprise a cell in a model non-human organism, a model non-human mammal that expresses a Cas protein, a mouse that expresses a Cas protein, a mouse that expresses Cpf1, a cell in vivo or a cell ex vivo or a cell in vitro (see e.g., WO 2014/093622; US Patent Publication Nos. 20120017290 and 20110265198; US Patent Publication No. 20130236946; Platt et al., "CRISPR-Cas9 Knockin Mice for Genome Editing and Cancer Modeling" Cell (2014), 159(2): 440-455; WO2014204723A1; WO2014204726A1; and WO2016049251). The cell(s) may also comprise a human cell. Mouse cell lines may include, but are not limited to neuro-2a cells and EL4 cell lines (ATCC TIB-39). Primary mouse T cells may be isolated from C57/BL6 mice. Primary mouse T cells may be isolated from Cas9-expressing mice.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (~10 sgRNAs/gene) may also be used in a mouse that expresses a Cas9 protein (see, e.g., WO2014204727A1). The cells of the mouse can then be analyzed using the methods of the present invention.

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus.

Applicants have developed and optimized methods and conditions for delivery of a CRISPR system to primary mouse T-cells. Applicants have achieved over 80% transduction efficiency with Lenti-CRISPR constructs in CD4 and CD8 T-cells. Despite success with lentiviral delivery, recent work by Hendel et al, (Nature Biotechnology 33, 985-989 (2015) doi:10.1038/nbt.3290) showed the efficiency of editing human T-cells with chemically modified RNA, and direct RNA delivery to T-cells via electroporation. In certain embodiments, perturbation in mouse primary T-cells may use these methods.

In certain embodiments, whole genome screens can be used for understanding the phenotypic readout of perturbing potential target genes. In preferred embodiments, perturbations target expressed genes as defined by RNA-seq using a focused sgRNA library. Libraries may be focused on expressed genes in specific networks or pathways. In other preferred embodiments, regulatory drivers are perturbed. In certain embodiments, Applicants perform systematic perturbation of key genes that regulate immune cell function in a high-throughput fashion. Applicants can use gene expression profiling data to define the target of interest and perform follow-up single-cell and population RNA-seq analysis. Not being bound by a theory, this approach will enhance the understanding of the biology of immune cells, and accelerate the development of therapeutics for human disorders, in particular autoimmune disease and cancer.

In certain embodiments, after determining Perturb-seq effects in primary T-cells, the cells are infused back to the tumor xenograft models (melanoma, such as B16F10 and colon cancer, such as CT26) to observe the phenotypic effects of genome editing. Not being bound by a theory, detailed characterization can be performed based on (1) the phenotypes related to tumor progression, tumor growth, immune response, etc. (2) the TILs that have been genetically perturbed by CRISPR-Cas9 can be isolated from tumor samples, subject to cytokine profiling, qPCR/RNA-seq, and single-cell proteomic analysis to understand the biological effects of perturbing the key driver genes within the tumor-immune cell contexts. Not being bound by a theory, this will lead to validation of TILs biology as well as lead to therapeutic targets.

With respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 August 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015).

Nishimasu et al., Crystal Structure of Staphylococcus aureus Cas9," Cell 162, 1113-1126 (Aug. 27, 2015).

Zetsche et al., "Cpf1 Is a Single RNA-Guided Endonuclease of a Class 2 CRISPR-Cas System," Cell 163, 1-13 (Oct. 22, 2015).

Shmakov et al., "Discovery and Functional Characterization of Diverse Class 2 CRISPR-Cas Systems," Molecular Cell 60, 1-13 (Available online Oct. 22, 2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Compressed Sensing

Mammalian genomes contain approximately 20,000 genes, and mammalian expression profiles are frequently studied as vectors with 20,000 entries corresponding to the abundance of each gene. It is often assumed that studying gene expression profiles requires measuring and analyzing these 20,000 dimensional vectors, but some mathematical results show that it is often possible to study high-dimensional data in low dimensional space without losing much of the pertinent information. In one embodiment of the present invention, less than 20,000 aptamers are used to detect protein expression in single cells. Not being bound by a theory, working in low dimensional space offers several advantages with respect to computation, data acquisition and fundamental insights about biological systems.

In one embodiment, aptamers are chosen for protein targets that are generally part of gene modules or programs, whereby detection of a protein allows for the ability to infer expression of other proteins present in a module or gene program. Samples are directly compared based only on the measurements of these signature genes.

In alternative embodiments, sparse coding or compressed sensing methods can be used to infer large amounts of data with a limited set of target proteins. Not being bound by a theory, the abundance of each of the 20,000 genes can be recovered from random composite measurements. In this regard, reference is made to Cleary et al., "Composite measurements and molecular compressed sensing for highly efficient transcriptomics" posted on Jan. 2, 2017 at biorxiv.org/content/early/2017/01/02/091926, doi.org/10.1101/091926, incorporated herein by reference in its entirety.

The present invention advantageously provides for multiplex detection of proteins in a plurality of single cells. The single cells may include cells of different cell type or states. The single cells may have been subject to different perturbations. The novel design of oligonucleotides linked to a solid support, including novel use of barcodes and aptamers, allows for a bulk sequencing readout of up to thousands of proteins in thousands of cells. Moreover, the present invention allows for quantification of proteins in single cells and coupling the protein expression to gene expression. The invention also advantageously allows detection of proteins and mRNA. Finally, interacting proteins in single cells may be identified.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Preparation of Oligonucleotide Labeled Solid Supports

Solid supports linked to oligonucleotides are prepared, such that each oligonucleotide comprises a cellular barcode shared by all oligonucleotides attached to the individual solid support. The solid support may be a bead or the surface of a microwell. In preferred embodiments, the solid support is a bead. Each oligonucleotide preferably includes a UMI to 'uniquely' define each oligonucleotide on the solid support. The oligonucleotides are conjugated to the solid support in a releasable fashion, for instance by a photocleavable linker, an enzymatically cleavable linker, chemically releasable linker. The linker may also include an acrylamide moiety in order to link the solid support comprising a hydrogel. In addition, the oligonucleotides contain a sequence for hybridization or ligation to a hybridization sequence of the aptamer-protein barcode oligonucleotide produced as described in Example 2. In one embodiment, the cellular barcode is generated by a split-pool protocol. The split-pool process may include any process described herein, such as, but not limited to the hybridization-extension protocol described in Klein et al. or by using sticky end ligation, thus yielding unique combinatorial cellular barcodes on each solid support. In the case of beads, beads are split into wells comprising different first barcode indices. After adding the first indices, the beads are pooled and split into wells comprising different second indices. In the case of microwell surfaces, different first indices are added to each well, followed by the addition of second indices, such that no two wells have the same combination of indices. The sticky end ligation can include more than one, preferably, more than two indices, each including more than 2 nucleotides and each having sticky ends compatible with ligation to the previous index. The number of indices can determine the number of cycles of split and pool ligation that are required to generate the desired number of unique barcodes.

The oligonucleotide sequences may be bonded, e.g., covalently, through primer extension, through ligation, or the like. Any of a wide variety of different techniques may be used, and those of ordinary skill in the art will be aware of many such techniques. The exact joining technique used is not necessarily critical, and can vary between embodiments. Non-limiting examples include ligases or other suitable techniques such as those discussed in U.S. Pat. Apl. Ser. No. 61/981,123, incorporated herein by reference.

The oligonucleotide may be of any suitable length or comprise any suitable number of nucleotides. The oligonucleotide may comprise DNA, RNA, and/or other nucleic acids such as PNA, and/or combinations of these and/or other nucleic acids. In some cases, the oligonucleotide is single stranded, although it may be double stranded in other cases.

In one embodiment, the solid support comprises a bead or surface linked to a ssDNA sequence oligonucleotide through a linker, an identical sequence for sequencing, a cell barcode sequence, an UMI, and a sequence for hybridization or ligation to the hybridization sequence of an aptamer oligonucleotide. The sequence for sequencing may include, but is not limited to a T7 promoter or a PCR priming site for library prep. In certain embodiments, the sequence for sequencing includes, but is not limited to the primer region for Illumina paired end library prep.

A solid support linked to oligonucleotides containing a cell barcode may be prepared for single cell analysis of target proteins according to the following steps (see e.g., FIG. 1A-H). The oligonucleotides may be synthesized as described herein. In one embodiment, the oligonucleotide sequence is synthesized as a ssDNA polynucleotide sequence. In preferred embodiments, the synthesized oligonucleotide has the structure comprising:

5'-/5Acryd/-[cleavable element]-[NXT1]-[barcode1]-[H1]-[barcode2]-[H2]-3'

The 5Acryd is an acrylamide moiety used to link the oligonucleotide to the solid support.

The [Cleavable element] can include, but is not limited to:
1) /iSpPC/Photocleavable linker, that can be released by UV irradiation.
2) /ideoxyU/Enzymatically cleavable linker wherein incorporation of several deoxyuridine, a base that can be removed by the enzyme uracil-N-deglycosylase (UNG), renders the oligo susceptible to strand scission by for, example, Endonuclease VIII.

The T7 RNA polymerase promoter sequence may be included for linear amplification if it is preferred over PCR.

NXT1 includes any primer sequence for sequencing library generation. In one embodiment, NXT1 includes, but is not limited to a primer sequence compatible with Illumina paired end sequencing library generation. NXT1 could serve as primers for PCR amplification. Extended primers could be used for incorporation of a sample specific barcode and Illumina flowcell binding if needed.

The cellular barcode sequence is represented by [Barcode 1] and [barcode2], but can include any combinatorially constructed barcode sequence. The barcode sequence described is generated by adding two indices to the oligonucleotide sequence by hybridization and extension as for Indrop (Klein et al. 2015), to generate unique cellular barcodes.

[Hybridization sequence 1] comprises any desired hybridization sequence, such that it hybridizes with [hybridization 2]. For Indrop this is a poly T stretch to capture mRNA. In certain embodiments, the solid surface further comprises the oligonucleotides comprising the poly T stretch for capturing mRNA and proteins.

Example 2: Preparation of Oligonucleotide Labeled Aptamers

Aptamers may be prepared for single cell analysis of target proteins according to the following steps (see e.g., custom synthesized aptamer oligo, FIG. 1G). The aptamers may be synthesized or commercially available as described herein. In one embodiment, the oligonucleotide sequence is synthesized as a ssDNA polynucleotide sequence. In one embodiment, the oligonucleotide sequence is a dsDNA polynucleotide sequence with an aptamer sequence linked to the 3' end of one strand. In preferred embodiments, the synthesized aptamer has the structure comprising:

5'-[aptamer]-[spacer]-[NXT2]-[UMI]-[Protein Barcode]-[H2*]-3'

The [spacer] can be any spacer that functions as an effective blocking agent against DNA polymerase extension to prevent turning the aptamer into a dsDNA molecule and interfering with target protein recognition. Exemplary spacers include, but are not limited to an internal C3 spacer (/iSpC3/) from IDTDNA.

[NXT2] is a primer region for library prep. In certain embodiments [NXT2] includes, but is not limited to the primer region for Illumina paired end library prep. The primer should be compatible with NXT1 (described herein for solid support oligonucleotides) such that a paired end amplification product can be generated by PCR.

A Unique molecular identifier (UMI) is included to bioinformatically correct for asymmetric amplification of any given oligonucleotide.

The [protein barcode] is an ~21 bp protein barcode unique to each aptamer used to identify the aptamer target.

The [H2*] sequence is an ~22 bp hybridization region for hybridization and extension coupling of the aptamer oligo to the solid support oligo. The hybridization sequence is complementary to an oligonucleotide sequence such that the aptamer oligonucleotide construct may hybridize to the oligonucleotide sequence linked to a solid support. The hybridized sequence may then be used as a priming site for extension, thus generating a dsDNA sequence linked to a solid support (FIG. 1H). In alternative embodiments, the hybridization sequence is used for ligation of the aptamer oligonucleotide sequence to the oligonucleotide linked to a solid support. In another embodiment, the aptamer sequence may include a reactive group, whereby upon activation of the reactive group, the aptamer will become covalently linked to a bound target protein. Not being bound by a theory, aptamers may have a high off rate for binding target proteins and incorporation of the reactive group prevents target proteins from dissociating from the aptamer. Target proteins may also dissociate from the aptamers during downstream processing. Not being bound by a theory, covalently linking the aptamer to the target protein prevents dissociating the interaction during downstream processing steps (e.g., isolating aptamer protein complexes). The reactive group may be a photoreactive group. In one embodiment, the reactive group may include, but is not limited to a 5-iododeoxyuridine, a diazirine moiety or an F-carboxyl group (see e.g., Vinkenborg, et al., 2012, Angew. Chem. Int. Ed., 51: 9176-9180. doi:10.1002/anie.201204174; Zhang et al., Royal Society of Chemistry accepted manuscript; and Wang, et al., Chem. Sci., 2016, 7, 2157-2161 DOI: 10.1039/ C5SC02631H). The step of covalently linking is preferably performed at any step following the incubating step and before isolating oligo-aptamer protein complexes. In preferred embodiments, the linking is performed after a step of washing away unbound proteins to avoid non-specific cross-linking to unbound proteins.

The aptamer oligonucleotide comprises a target specific barcode which encodes and thus identifies the aptamer and its corresponding target in a sequencing readout. Additionally, the oligonucleotide includes a sequence which allows for amplification during library preparation. In one embodiment, the sequence is a forward or reverse priming site for amplification by PCR (NXT1 & NXT2 in FIG. 1). NXT 1 and NXT2 may consist of a mixture of 'staggered' oligonucleotides to prevent all library members from having the same base in any given sequencing cycle and making cluster identification difficult, as described herein. By staggering, the sequences are offset compared to one another by one, two or three base pairs. The sequence for priming PCR is between the aptamer and target barcode sequence, such that the amplification product includes the target barcode sequence. The aptamer oligonucleotide also includes a hybridization sequence (FIG. 1G, H2) to allow hybridization to a complementary sequence on the oligonucleotide linked to the solid support, such that during preparation of the solid support dsDNA may be generated by extension with a DNA polymerase. The hybridization sequence may also be a dsDNA segment configured with an overhang capable of hybridization with a complementary sequence on the oligonucleotide linked to the solid support such that the oligonucleotides may be ligated (example FIGS. 2 G, H). In one embodiment, the hybridization sequence is a ssDNA overhang.

In one embodiment, the target protein barcode is ligated or conjugated to the 3' end of the aptamer. The target protein barcode sequence may be made dsDNA, such that there is no interference with the structure of the aptamer, and target recognition is not disturbed. In one embodiment, the aptamer oligonucleotide comprises a hybridization sequence, a dsDNA sequence comprising the target specific barcode, the sequence which allows amplification during library preparation, and an aptamer specific for the target protein ligated to the dsDNA sequence. In one embodiment, the hybridization sequence is a ssDNA overhang. In one embodiment, the aptamer oligonucleotide is a ssDNA sequence comprising a hybridization sequence, a target specific barcode, a sequence which allows amplification during library preparation, a spacer to prevent DNA polymerase extension of the aptamer sequence, and an aptamer specific for the target protein.

Example 3: Preparation of Oligonucleotide and Aptamer Labeled Beads

Aptamers are chosen based on the target proteins to be detected. The target proteins may be related by a common pathway or function. The target proteins may be selected based on known gene expression patterns of the cells to be tested. Tens of target proteins may be detected in a readout panel. Alternatively, hundreds or thousands of target proteins may be detected in a readout panel. Not being bound by a theory, a single bead may accommodate multiple copies of thousands of unique aptamers, each specific for a different target protein. Once each of the aptamers in a chosen readout panel is modified in accordance to Example 2, the aptamer-protein barcode oligonucleotides for that panel can be pooled, either in an equimolar ratio, or in any desired alternative ratio that could for instance minimize readout of overly abundant proteins, or inversely, promote capture of lowly expressed targets. The aptamers may be chosen based on expression levels, such that beads with aptamers for only lowly expressing target proteins are prepared. Alternative beads may be prepared with aptamers specific for abundant proteins. This pool can subsequently be hybridized followed by extension or ligated to a pool of solid supports, which were prepared as in Example 1.

Example 4: Single Cell Detection of Protein Targets

The solid supports, as prepared in Example 3, are co-encapsulated with single cells in a microfluidic drop or microwell in the case of beads or have a cell sorted in the case of a microwell surface, such that the cells are lysed upon co-encapsulation or sorting in a buffer that does not disturb recognition by the aptamer. After incubation to allow for aptamer-target recognition and binding, the droplet emulsion is broken, or in a microwell settings beads are spun out of the wells, or for surfaces liquid removed, and unbound proteins may be washed away. In alternative embodiments, the linkers are cleaved before incubation allowing the oligonucleotides to freely bind their targets. Incubation times may vary according to the aptamers conjugated to the beads and the incubation conditions. In certain embodiments, the droplets are incubated between 4°-10° C. In certain embodiments, the droplets are incubated for between 0.5 and 24 hours. One skilled in the art can adjust incubation times and temperatures in order to optimize binding. Additionally, one skilled in the art would know to adjust buffer conditions, such as, but not limited to adding detergent to the lysis buffer in order to prevent non-specific binding, adding bovine serum albumin (BSA), or adding salmon sperm. Alternatively, the wash buffers may be adjusted to decrease non-specific binding. A succession of buffers comprising increasing ionic strength and/or detergent may be used during washing steps. The oligonucleotide-aptamer-protein complex may be released from the beads by cleaving the linker described in Example 1. This release also releases oligonucleotide-aptamer molecules that did not bind a target protein (e.g., the protein is not expressed in a cell), and this step is performed at a dilution that minimizes cross talk between the oligonucleotide-aptamer molecules with the oligonucleotide-aptamer-protein complexes.

Subsequently, oligonucleotide-aptamer-protein complexes are isolated from the oligonucleotide-aptamer molecules by specifically binding proteins. In certain embodiments, complexes are isolated by biotinylation of primary amine groups, followed by streptavidin bead purification, or with carboxylate functionalized beads. Once the oligonucleotide-aptamer-protein complexes are isolated, the part of the oligonucleotide containing the "Protein barcode-Cellular barcode-UMI" information is amplified and prepared for a sequencing readout. Proteins could be denatured in this step to release the oligonucleotide-aptamer part and make it available for nucleic acid cleanup and library prep. In certain embodiments, such as detecting only proteins, low pass sequencing is required. In other embodiments, such as detecting protein and RNA, deep sequencing may be required.

Exemplary Single-Cell NGS Proteomics Protocol:

In one embodiment, the proteomic assay of the present invention builds upon the single-cell RNA-seq method described for inDrop (Klein et al., 2015) and includes novel alterations to accommodate protein capture, isolation of oligonucleotide-protein complexes and identification of proteins.

As for the inDrop approach, hydrogel beads are prepared and loaded with the custom oligonucleotides as described herein.

1) Using a microfluidic setup similar to inDrop, droplets are generated that upon co-encapuslation lyses a single cell in the presence of an aptamer functionalized hydrogel bead. In certain embodiments, the aptamers were selected on recombinant proteins in solution, thus a non-denaturing lysis buffer is used to maintain conformational stability and aptamer-target recognition.

In one embodiment, the oligonucleotides remain affixed to the hydrogel bead while in the droplet. This embodiment is described by steps 2a to 7a.

2a) The droplets are incubated at 37° C. for 2 h to increase diffusion of proteins in the droplet, followed by an overnight incubation at 4° C. to further allow target-aptamer encounters and minimize the off-rate of the aptamers.

3a) This is followed by breaking of the emulsion as described previously, and extensive washing of the hydrogels in a cold washing buffer to wash away unbound (non-targeted) proteins.

4a) Next, the captured target proteins that are in a aptamer-target protein complex are chemically biotinylated using standard methods targeting primary amines on the proteins while on ice for 2 h, or at an experimentally defined temperature and duration that maximizes protein recovery. After the reaction, primary amines are added to neutralize the NHS esters, and free floating unbound biotin is washed away, while the beads with biotinylated protein-aptamer complexes are maintained.

5a) Next, the protein-aptamer complexes are released from the hydrogels either by photocleavage or enzymatic release.

6a) Next, protein-aptamer complexes are purified using streptavidin beads, washing away non-protein bound aptamers.

7a) Proteins are denatured to release the aptamer-oligo, which will then be amplified for next generation sequencing library prep. In one embodiment, PCR amplification with Nextera™ primers is performed, generating sequenceable samples that will result in sequencing the protein barcode, the cellular barcode and the UMI.

In one embodiment, the oligonucleotides are released from the hydrogel to freely diffuse and find their target protein in the droplet. This embodiment is described by steps 2b to 5b.

2b) The aptamer oligonucleotides are released in the drop either by photocleavage or enzymatic release to improve aptamer-target protein interactions. The droplets are incubated at 37° C. for 2 h to increase diffusion of proteins in the droplet, followed by an overnight incubation at 4° C. to further allow target-aptamer encounters and minimize the off-rate of the aptamers.

3b) This is followed by breaking of the emulsion as described previously, the aqueous phase is preserved and all proteins are chemically biotinylated using standard methods targeting primary amines while on ice for 2 h, or at an experimentally defined temperature and duration that maximizes protein recovery. After the reaction, primary amines are added to neutralize the NHS esters.

4b) Next, protein-aptamer complexes and non-target proteins are purified using streptavidin beads, washing away non-protein bound aptamers.

5b) Proteins are denatured to release the aptamer-oligonucleotide, which will then be amplified for next generation sequencing library prep. The most straightforward approach would be to PCR amplify with Nextera™ primers, generating sequenceable samples that will result in sequencing the protein barcode, the cellular barcode and the UMI.

In alternative embodiments, the cellular barcode construct may be dsDNA or ssDNA. Not being bound by a theory, dsDNA is preferred in terms of stability and dsDNA is less likely to interfere with aptamer target recognition. Not being bound by a theory, dsDNA can suffer from increased binding by proteins that are not aptamer specific, and this effect could be less if ssDNA would be used. When ssDNA is preferable, the aptamer oligonucleotide is added to the cellular barcode by a splint ligation reaction instead of a DNA polymerase extension reaction. Splint ligation relies upon the ability of T4 DNA ligase to covalently join the terminal 3'-hydroxyl group of an RNA molecule to the labeled 5'-phosphate group of a DNA chain in the presence of a DNA "splint" or "bridge" oligonucleotide that is complementary to both (see e.g., Kershaw and O'Keefe, 2012, Splint Ligation of RNA with T4 DNA Ligase. Recombinant and In Vitro RNA Synthesis, Volume 941 of the series Methods in Molecular Biology pp 257-269).

In certain embodiments, aptamers can be equipped with a reactive group to covalently link the aptamer oligo to the protein (see e.g., Vinkenborg, et al., 2012, Angew. Chem. Int. Ed., 51: 9176-9180. doi:10.1002/anie.201204174; Zhang et al., Royal Society of Chemistry accepted manuscript; and Wang, et al., Chem. Sci., 2016, 7, 2157-2161 DOI: 10.1039/C5SC02631H) In preferred embodiments, the reactive group is a photoreactive group. Not being bound by a theory, this allows for more stringent washing and purification conditions as there is no risk of breaking up the target protein-aptamer bond.

Example 5: Oligonucleotides for Protein and mRNA Measurements

The present invention may also be used to measure a single-cell proteome and transcriptome. Solid supports can be made multifunctional, i.e. the beads contain additional oligonucleotides including a Cellular barcode-UMI and a poly T sequence instead of an aptamer to simultaneously capture cellular polyadenylated mRNA. The oligonucleotides may comprise any previously described barcoded oligonucleotides and the solid support may comprise any previously described bead or solid support. The oligonucleotides for capturing mRNA may be prepared as previously described. In one embodiment, oligonucleotides linked to a solid support for capturing mRNA and proteins are identical except for the hybridization sequence 1. In one embodiment, a pool of oligonucleotides for generating barcode 2 and hybridization sequence 1 are prepared in order to obtain the desired ratios of oligonucleotides for capturing proteins and mRNA. For capturing mRNA the oligonucleotides comprise a poly T sequence and for capturing proteins the oligonucleotides comprise a hybridization 1 sequence complementary to hybridization 2 on the aptamer labeled oligonucleotides. The barcode 2 sequence is the same for both of these oligonucleotides. The ratio of these oligonucleotides may be varied to obtain the desired ratio on a solid support. Such oligonucleotides may be synthesized as an index pair comprising the same barcode, followed by synthesis of a poly T sequence or hybridization 2 sequence. After synthesis, an index for generating the solid support is obtained after pooling the synthesized oligonucleotides. Each subsequent index may be similarly synthesized and pooled.

In one embodiment, the solid support is a bead. In a preferred embodiment, the beads are hydrogel beads. Beads of the present invention may include up to billions of linked oligonucleotide molecules. Therefore, for co-measurements of mRNA and protein from a single cell the bead may comprise oligonucleotides for capturing mRNA and proteins at a tailored ratio. The oligonucleotides for mRNA and proteins may additionally comprise different linkers, such that the different oligonucleotides may be released at different times, and processed separately for optimal biomolecular library preparation.

In one embodiment, mRNA and proteins are simultaneously measured in single cells using the beads as described above and droplets formed by microfluidics or solid supports. In preferred embodiments, linkers specific for oligonucleotides for mRNA capture are cleaved in droplets or solid supports, such that these oligonucleotides are released and hybridize to mRNA molecules. In one embodiment, a reverse transcription step is performed in the droplet to generate cDNA after release from the bead. Not being bound by a theory, cDNA is more stable than mRNA and performing RT-PCR immediately after capture improves recovery of gene expression data. Not being bound by a theory, protein is more stable than mRNA, but requires incubation to be captured by aptamers. After cDNA production, the droplets may be incubated at a temperature and for a period of time required for capture by aptamers. In certain embodiments, the droplets are incubated between 4°-10° C. In certain embodiments, the droplets are incubated for between 0.5 and 24 hours.

Example 6: Oligonucleotides for Protein-mRNA Measurements

Figure 3:
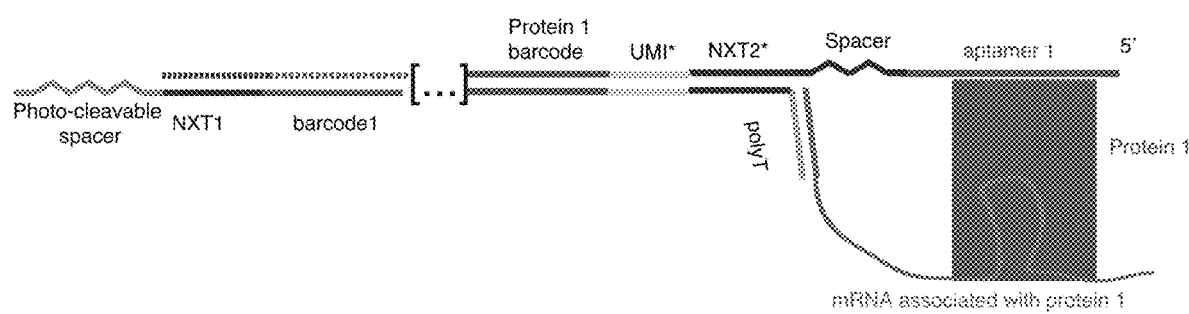
FIG. 3 illustrates an oligonucleotide for determining protein mRNA interactions. The oligonucleotide is synthesized as in FIG. 1 except the custom synthesized aptamer oligonucleotide comprising a complementary hybridization 2 sequence, protein barcode, sequencing primer NXT2, spacer, and aptamer is hybridized to a complementary oligonucleotide sequence, wherein the hybridization 2 sequence remains ssDNA and the sequence includes a poly T capture sequence. Upon binding of a protein-mRNA complex, the poly A tail of the mRNA may hybridize to the poly T sequence. Reverse transcription using the poly T sequence as a primer results in a sequence including both barcodes and mRNA sequence.

The present invention may also be used to measure single-cell protein-mRNA interactions. In one embodiment, the aptamer is ligated to one strand of a dsDNA oligonucleotide. The other strand may comprise a poly T sequence, creating a Y-oligonucleotide construct (FIG. 3). Beads or solid supports prepared with the Y-oligonucleotide bind a target protein through an aptamer. The target protein may be a part of a protein-mRNA complex. Therefore, the associated mRNA can hybridize to the poly T strand of the Y-oligonucleotide. Reverse transcription of the mRNA using the poly T hybridization as a primer results in a sequence comprising a cell barcode, UMI, aptamer barcode and cDNA. Even though any non-protein bound mRNA molecule could in principle bind the polyT sequence, mRNA molecules typically associated with the target protein will be enriched due to its proximity.

In one embodiment, non-interacting mRNAs are captured by the Y-oligonucleotide in order to detect protein and mRNA expression.

Example 7: Oligonucleotides for Protein Complex Measurements

The present invention may also be used to measure single-cell protein-protein interactions. In one embodiment, the aptamer is ligated to one strand of a dsDNA oligonucleotide. The other strand may comprise a universal hybridization sequence, creating a Y-oligonucleotide construct (FIG. 2). Beads or solid supports prepared with the Y-oligonucleotide bind a target protein through an aptamer. The target protein may be a part of a protein complex (or multiple interacting proteins). Therefore, interacting proteins are also bound to the Y-oligonucleotide in which the aptamer of the Y molecule recognizes one of the proteins in the complex. The other proteins of the complex are exposed to a separate set of aptamers. This new set of aptamers is prepared to contain an amplification sequence, a protein barcode and a hybridization sequence for ligation to the Y-oligonucleotide. The hybridization sequence hybridizes to the universal hybridization sequence if an interaction occurs. Not being bound by a theory, the universal hybridization sequence is short in order to prevent hybridization in the absence of an interaction. An amplified library containing constructs that include a cell barcode, UMI, first and second aptamer barcode is sequenced. Thus, pairwise interactions in single cells may be detected.

FIG. 2 depicts one embodiment for an oligonucleotide construct for measuring protein complexes at the single cell level in an aptamer library×aptamer library fashion. The strand that doesn't contain the aptamer for protein A contains a hybridization 3 sequence [H3*]. After capture of protein complex protein 1-protein 2 based on aptamer 1, the complex is stained with a second set of aptamers. The second set of aptamers has a format comprising [aptamer]-[spacer]-[NXT3]-[protein 2 barcode]-[H3]. This allows for hybridization to [H3*] and polymerase extension to generate an oligo coding for both protein barcodes, cellular barcode, UMI and primers (NXT1 & NXT3) for library prep.

In one embodiment, beads and microfluidic droplets are used. The beads are co-encapsulated with single cells, and incubated in order to capture proteins on the Y-oligonucleotides. The droplets are broken and the beads are isolated, washing away unbound proteins. The samples are then incubated with the second set of aptamers. DNA extension is performed and sequencing libraries constructed.

The invention is further described by the following numbered paragraph:

1. An oligonucleotide-adorned solid support for the identification of proteins expressed in single cells, wherein said solid support comprises a plurality oligonucleotides, wherein each of said oligonucleotides comprise:

(a) a linker directly attached to the solid support;

(b) an identical sequence for use as a sequencing priming site;

(c) a uniform or near-uniform cell barcode sequence, wherein the uniform or near-uniform cell barcode sequence is the same across all oligonucleotides on said solid support, but varies among the oligonucleotides on any other individual solid support;

(d) a uniform or near-uniform target barcode sequence, wherein the uniform or near-uniform target barcode sequence is specific to an individual aptamer; and (e) an aptamer specific to the target barcode sequence configured for binding to a target protein, wherein the solid support binds to a plurality of target proteins, and wherein the solid support comprises more than one copy of oligonucleotides specific for each of the plurality of target proteins.

2. The oligonucleotide-adorned solid support according to paragraph 1, wherein the copy number of oligonucleotides specific for different target proteins on said solid support are varied, whereby the solid support comprises a desired ratio of aptamers.

3. The oligonucleotide-adorned solid support according to paragraphs 1 or 2, wherein each oligonucleotide further comprises a Unique Molecular Identifier (UMI) which differs for each oligonucleotide.

4. The oligonucleotide-adorned solid support according to any of paragraphs 1 to 3, further comprising a spacer between the aptamer and the oligonucleotide strand conjugated to said aptamer, wherein the spacer functions as a blocking agent against DNA polymerase extension.

5. The spacer according to paragraph 4, wherein said spacer comprises a C3 spacer.

6. The oligonucleotide-adorned solid support according to any of paragraphs 1 to 5, wherein the UMI comprises 6 to 20 nucleotides in length.

7. The oligonucleotide-adorned solid support according to any of paragraphs 1 to 6, wherein each barcode ranges from 4 to 100 nucleotides in length.

8. The oligonucleotide-adorned solid support according to any of paragraphs 1 to 7, wherein the linker is chemically-cleavable, enzymatically cleavable, or photocleavable.

9. The oligonucleotide-adorned solid support according to any of paragraphs 1 to 8, wherein said aptamers further comprise a photoreactive group configured to covalently link the aptamers to captured proteins upon experimentally defined illumination.

10. The oligonucleotide-adorned solid support according to any of paragraphs 1 to 9, wherein said oligonucleotides further comprise a reverse priming site after the target barcode sequence, whereby by the cell and target barcodes may be amplified by PCR.

11. The oligonucleotide-adorned solid support according to any of paragraphs 1 to 10, wherein the solid support is a bead.

12. The oligonucleotide-adorned solid support according to paragraph 11, wherein the bead is a magnetic bead.

13. The oligonucleotide-adorned solid support according to paragraph 11, wherein the bead is a deformable bead.

14. The oligonucleotide-adorned solid support according to paragraph 11, wherein the bead is a hydrogel bead.

15. The oligonucleotide-adorned solid support according to any of paragraphs 1 to 10, wherein the solid support is a surface of a microwell.

16. The microwell surface according to paragraph 15, wherein the surface comprises a hydrogel surface.

17. The oligonucleotide-adorned solid support according to any of paragraphs 1 to 16, wherein said oligonucleotides further comprise a 6 to 12 nucleotide universal hybridization sequence on the opposite DNA strand as the aptamer, wherein said universal hybridization sequence is complementary to a hybridization sequence linked to a set of second oligonucleotide linked affinity reagents comprising an aptamer, antibody or antibody fragment.

18. The oligonucleotide-adorned solid support according to any of paragraphs 1 to 16, wherein said oligonucleotides further comprise a poly T sequence on the opposite DNA strand as the aptamer, whereby the oligonucleotides are configured to capture polyadenylated mRNA.

19. The oligonucleotide-adorned solid support according to any of paragraphs 1 to 16, further comprising a plurality of second oligonucleotides on said solid support, said second oligonucleotides comprising:

(a) a linker directly attached to the solid support;

(b) an identical sequence for use as a sequencing priming site;

(c) a uniform or near-uniform cell barcode sequence, wherein the uniform or near-uniform cell barcode sequence is the same across all oligonucleotides on said solid support, but varies among the oligonucleotides on any other individual solid supports; and (d) an oligonucleotide redundant sequence for capturing polyadenylated mRNAs and priming reverse transcription, whereby the solid support is configured to bind proteins and mRNAs.

20. The oligonucleotide-adorned solid support according to paragraph 19, wherein the oligonucleotide sequence for capturing polyadenylated mRNAs and priming reverse transcription is an oligo dT sequence.

21. The oligonucleotide-adorned solid support according to any of paragraphs 19 to 20, wherein each second oligonucleotide comprises a Unique Molecular Identifier (UMI) which differs for each oligonucleotide.

22. The oligonucleotide-adorned solid support according to paragraph 21, wherein the UMI comprises 6 to 20 nucleotides in length.

23. The oligonucleotide-adorned solid support according to any of paragraphs 19 to 22, wherein each second oligonucleotide barcode ranges from 4 to 100 nucleotides in length.

24. The oligonucleotide-adorned solid support according to any of paragraphs 19 to 23, wherein the second oligonucleotide linker is chemically-cleavable, enzymatically cleavable, or photocleavable.

25. The oligonucleotide-adorned solid support according to paragraph 24, wherein the second oligonucleotide linker is differentially cleavable as compared to the aptamer oligonucleotide linker, whereby each linker is capable of cleavage at different times.

26. The oligonucleotide-adorned solid support according to any of paragraphs 19 to 25, wherein the copy number of oligonucleotides specific for different target proteins and second oligonucleotides on said solid support are varied, whereby the solid support comprises a desired ratio of oligonucleotides for capturing proteins and mRNAs.

27. The oligonucleotide-adorned solid support according to paragraph 26, wherein the second oligonucleotides comprise 1-5% of oligonucleotides on said solid support and the oligonucleotides specific for different target proteins comprise 95-99% of oligonucleotides on said solid support.

28. A method of identifying proteins expressed in single cells comprising:

(a) segregating single cells with a solid support according to any of paragraphs 1 to 16 by a method comprising merging one uniquely barcoded bead with a single-cell in an emulsion droplet, microfluidic drop, or microwell, or a method comprising adding a single cell to a microwell comprising a barcoded surface;

(b) lysing the cells and cleaving the linkers in a buffer that preserves aptamer-target recognition;

(c) incubating the lysed cells and oligonucleotides thereby capturing expressed aptamer target proteins on the cleaved oligonucleotides;

(d) pooling the samples after breaking droplets or pooling the samples from microwells;

(e) optionally, functionalizing proteins;

(f) isolating oligo-aptamer protein complexes; and (g) preparing and sequencing a single composite sequencing library, whereby the cell barcodes record the cell-of-origin of each oligonucleotide sequence and target barcodes record expressed proteins from the same cell.

29. The method according to paragraph 28, wherein the proteins are functionalized with biotin.

30. The method according to paragraph 29, wherein isolating oligo-aptamer protein complexes comprises streptavidin bead purification.

31. The method according to paragraph 28, wherein isolating oligo-aptamer protein complexes comprises conjugation of proteins to functionalized beads.

32. A method of identifying proteins expressed in single cells comprising:

(a) segregating single cells with a solid support according to any of paragraphs 1 to 16 by a method comprising merging one uniquely barcoded bead with a single-cell in an emulsion droplet, microfluidic drop, or microwell, or a method comprising adding a single cell to a microwell comprising a barcoded surface, wherein the cells are lysed in a buffer that preserves aptamer-target recognition;

(b) incubating the lysed cells with the beads or surfaces thereby capturing expressed aptamer target proteins on each bead or surface;

(c) wherein beads are used, breaking droplets or isolating beads from microwells and pooling the beads in solution;

(d) washing the beads or surfaces, wherein unbound proteins are removed;

(e) cleaving the linkers;

(f) isolating oligo-aptamer protein complexes from oligo-aptamer molecules; and (g) preparing and sequencing a single composite sequencing library, whereby the cell barcodes record the cell-of-origin of each oligonucleotide sequence and target barcodes record expressed proteins from the same cell.

33. The method according to paragraph 32, wherein the method further comprises covalently linking the aptamers to captured proteins after washing the beads or surfaces.

34. The method according to paragraph 32 or 33, wherein the method further comprises functionalizing proteins after washing the beads or surfaces or after covalently linking the aptamers to captured proteins.

35. The method according to paragraph 34, wherein said linkers are cleaved enzymatically, chemically or by UV treatment and said functionalizing proteins is performed before said cleavage.

36. The method according to paragraph 34, wherein said linkers are cleaved chemically or by UV treatment and said functionalizing proteins is performed after said cleavage.

37. The method according to any of paragraphs 34 to 36, wherein proteins are functionalized with biotin.

38. The method according to paragraph 37, wherein isolating oligo-aptamer protein complexes from oligo-aptamer molecules comprises streptavidin bead purification.

39. The method according to paragraph 32 or 33, wherein isolating oligo-aptamer protein complexes from oligo-aptamer molecules comprises conjugation of proteins to functionalized beads.

40. A method of identifying proteins and mRNAs expressed in single cells comprising:

(a) segregating single cells with a solid support according to any of paragraphs 25 to 27, wherein the cells are lysed in a buffer that preserves aptamer-target recognition;

(b) incubating the lysed cells thereby capturing expressed aptamer target proteins and mRNAs on the first and second oligonucleotides;

(c) separating the first oligonucleotides from the second oligonucleotides;

(d) performing a reverse transcription reaction on the second oligonucleotides, whereby cDNA is obtained;

(e) isolating oligo-aptamer protein complexes from the first oligonucleotides; and (f) preparing and sequencing a single composite sequencing library for each of oligo-aptamer protein complexes and cDNA, wherein the second oligonucleotides are cleaved from the solid support before step (c), wherein the first oligonucleotides are cleaved after step (c) and before step (e).

41. The method according to paragraph 40, wherein segregating comprises merging one uniquely barcoded bead with a single-cell in an emulsion droplet, microfluidic drop, or microwell, wherein after step (b) droplets are broken or beads are isolated from microwells and the beads are pooled in solution, optionally wherein step (c) comprises separating supernatants comprising cleaved second oligonucleotides, optionally wherein the beads are washed before cleavage of the second and/or first oligonucleotides.

42. The method according to paragraph 40, wherein segregating comprises adding a single cell to a microwell comprising a barcoded surface, optionally wherein step (c) comprises separating supernatants comprising cleaved second oligonucleotides, optionally wherein the surfaces are washed before cleavage of the second and/or first oligonucleotides.

43. The method according to paragraphs 41 to 42, wherein the method further comprises covalently linking the aptamers to captured proteins after washing the beads or surfaces.

44. The method according to any of paragraphs 41 to 43, wherein the method further comprises functionalizing proteins after washing the beads or surfaces or after covalently linking the aptamers to captured proteins.

45. The method according to paragraph 44, wherein said first or second linkers are cleaved enzymatically, chemically or by UV treatment and said functionalizing proteins is performed before said cleavage.

46. The method according to paragraph 44, wherein said first or second linkers are cleaved chemically or by UV treatment and said functionalizing proteins is performed after said cleavage.

47. The method according to any of paragraphs 44 to 46, wherein proteins are functionalized with biotin.

48. The method according to paragraph 47, wherein isolating oligo-aptamer protein complexes from oligo-aptamer molecules comprises streptavidin bead purification.

49. The method according to any of paragraphs 40 to 43, wherein isolating oligo-aptamer protein complexes from the first oligo-aptamer molecules comprises conjugation of proteins to functionalized beads.

50. A method of identifying proteins and mRNAs expressed in single cells comprising:
   (a) segregating single cells with a solid support according to any of paragraphs 25 to 27 by a method comprising merging one uniquely barcoded bead with a single-cell in an emulsion droplet, microfluidic drop, or microwell, or a method comprising adding a single cell to a microwell comprising a barcoded surface, wherein the cells are lysed in a buffer that preserves aptamer-target recognition;
   (b) incubating the lysed cells thereby capturing expressed aptamer target proteins and mRNAs on the beads or surfaces;
   (c) wherein beads are used, breaking droplets or isolating beads from microwells and pooling the beads in solution;
   (d) washing the beads or surfaces, wherein unbound proteins are removed;
   (e) cleaving the second oligonucleotide linkers;
   (f) separating the supernatant comprising second oligonucleotides from the beads or surfaces;
   (g) performing a reverse transcription reaction on the supernatant, whereby the mRNA is converted to first strand cDNA;
   (h) cleaving the aptamer oligonucleotide linkers;
   (i) isolating oligo-aptamer protein complexes; and
   (j) preparing and sequencing a single composite sequencing library for each of oligo-aptamer protein complexes and cDNA.

51. A method of identifying proteins and mRNAs expressed in single cells comprising:
   (a) segregating single cells with a solid support according to any of paragraphs 19 to 27 by a method comprising merging one uniquely barcoded bead with a single-cell in an emulsion droplet, microfluidic drop, or microwell, or a method comprising adding a single cell to a microwell comprising a barcoded surface, wherein the cells are lysed in a buffer that preserves aptamer-target recognition;
   (b) incubating the lysed cells thereby capturing expressed aptamer target proteins and mRNAs on the beads or surfaces;
   (c) wherein beads are used, breaking droplets or isolating beads from microwells and pooling the beads in solution;
   (d) washing the beads or surfaces, wherein unbound proteins are removed;
   (e) performing a reverse transcription reaction, whereby the mRNA is converted to first strand cDNA, optionally, performing a reverse transcription reaction comprising alkyne functionalized nucleotides, whereby the mRNA is converted to biotinylated first strand cDNA;
   (f) cleaving the linkers;
   (g) isolating oligo-aptamer protein complexes, and optionally cDNA by a method comprising streptavidin bead purification; and
   (h) preparing and sequencing a single composite sequencing library, optionally preparing and sequencing a single composite sequencing library for each of oligo-aptamer protein complexes and cDNA.

52. The method according to paragraph 50 or 51, wherein the method further comprises covalently linking the aptamers to captured proteins after washing the beads or surfaces.

53. The method according to any of paragraphs 50 to 52, wherein the method further comprises functionalizing proteins after washing the beads or surfaces or after covalently linking the aptamers to captured proteins.

54. The method according to paragraph 53, wherein said first or second linkers are cleaved enzymatically, chemically or by UV treatment and said functionalizing proteins is performed before said cleavage.

55. The method according to paragraph 53, wherein said first or second linkers are cleaved chemically or by UV treatment and said functionalizing proteins is performed after said cleavage.

56. The method according to any of paragraphs 53 to 55, wherein proteins are functionalized with biotin.

57. The method according to paragraph 56, wherein isolating oligo-aptamer protein complexes from oligo-aptamer molecules comprises streptavidin bead purification.

58. The method according to any of paragraphs 50 to 52, wherein isolating oligo-aptamer protein complexes from oligo-aptamer molecules comprises conjugation of proteins to functionalized beads.

59. A method of identifying proteins and mRNAs expressed in single cells comprising:
   (a) segregating single cells with a solid support according to any of paragraphs 19 to 27 by a method comprising merging one uniquely barcoded bead with a single-cell in an emulsion droplet, microfluidic drop, or microwell, or a method comprising adding a single cell to a microwell comprising a barcoded surface;
   (b) lysing the cells and cleaving the linkers in a buffer that preserves aptamer-target recognition;
   (c) incubating the lysed cells thereby capturing expressed aptamer target proteins and mRNAs on the cleaved oligonucleotides;
   (d) pooling the samples after breaking droplets or pooling the samples from microwells;
   (e) optionally, functionalizing proteins;
   (f) isolating oligo-aptamer protein complexes;
   (g) performing a reverse transcription reaction, whereby the mRNA is converted to first strand cDNA; and
   (h) preparing and sequencing a single composite sequencing library for each of oligo-aptamer protein complexes and cDNA.

60. The method according to paragraph 59, wherein proteins are functionalized with biotin.

61. The method according to paragraph 60, wherein isolating oligo-aptamer protein complexes from oligo-aptamer molecules comprises streptavidin bead purification.

62. The method according to paragraph 59, wherein isolating oligo-aptamer protein complexes from oligo-aptamer molecules comprises conjugation of proteins to functionalized beads.

63. A method of identifying proteins that are in proximity in single cells comprising:
   (a) segregating single cells with a single solid support according to paragraph 17 by a method comprising merging one uniquely barcoded bead with a single-cell in an emulsion droplet, microfluidic drop, or microwell or a method comprising adding a single cell to a microwell comprising a barcoded surface, wherein the cells are lysed in a buffer that preserves aptamer-target recognition;
   (b) incubating the lysed cells thereby capturing oligo-aptamer protein complexes on the beads or surfaces;
   (c) wherein beads are used, breaking droplets or isolating beads from microwells and pooling the beads in solution;
   (d) washing the beads or surfaces, wherein unbound proteins are removed;
   (e) incubating the captured oligo-aptamer protein complexes with a set of second oligonucleotide linked affinity reagents comprising i) an aptamer, antibody or antibody fragment, ii) a sequencing primer sequence, iii) a target barcode and iv) a 6 to 12 nucleotide hybridization sequence, wherein when a second affinity reagent binds to an interacting protein the hybridization sequence binds to the universal hybridization sequence;

(f) washing the beads or surfaces, wherein unbound second affinity reagents are removed;

(g) performing DNA polymerase extension using the dsDNA hybridization region as a primer, whereby a DNA strand is synthesized comprising the barcodes corresponding to both proteins; and (h) preparing and sequencing a single composite sequencing library, whereby the cell barcodes record the cell-of-origin of each oligonucleotide sequence and target barcodes record the proteins in proximity.

64. A method of identifying post translationally modified proteins expressed in single cells comprising:

(a) segregating single cells with a single solid support according to paragraph 17 by a method comprising merging one uniquely barcoded bead with a single-cell in an emulsion droplet, microfluidic drop, or microwell or a method comprising adding a single cell to a microwell comprising a barcoded surface, wherein the cells are lysed in a buffer that preserves aptamer-target recognition;

(b) incubating the lysed cells thereby capturing expressed aptamer target proteins on the beads or surfaces;

(c) wherein beads are used, breaking droplets or isolating beads from microwells and pooling the beads in solution;

(d) washing the beads or surfaces, wherein unbound proteins are removed;

(e) incubating the captured oligo-aptamer protein complexes with a set of second oligonucleotide linked affinity reagents specific for target post translational modifications comprising i) an aptamer, antibody or antibody fragment, ii) a sequencing primer sequence, iii) a target barcode and iv) a 6 to 12 nucleotide hybridization sequence, wherein when an affinity reagent binds to a post translational modification on a captured protein the hybridization sequence binds to the universal hybridization sequence;

(f) washing the beads or surfaces, wherein unbound affinity reagents are removed;

(g) performing DNA polymerase extension using the dsDNA hybridization region as a primer, whereby a DNA strand is synthesized comprising the barcodes corresponding to both target protein and target post translational modification; and (h) preparing and sequencing a single composite sequencing library, whereby the cell barcodes record the cell-of-origin of each oligonucleotide sequence and target barcodes record the target protein and target post translational modification.

65. A method of identifying proteins and mRNAs expressed in single cells comprising:

(a) segregating single cells with a single solid support according to paragraph 18 by a method comprising merging one uniquely barcoded bead with a single-cell in an emulsion droplet, microfluidic drop, or microwell or a method comprising adding a single cell to a microwell comprising a barcoded surface;

(b) lysing the cells and cleaving the linkers in a buffer that preserves aptamer-target recognition;

(c) incubating the lysed cells and oligonucleotides thereby capturing expressed aptamer target proteins and mRNAs on the cleaved oligonucleotides;

(d) wherein beads are used, pooling the samples after breaking droplets or pooling the samples from microwells;

(e) optionally, functionalizing proteins;

(f) isolating oligo-aptamer protein complexes from oligo-aptamer molecules;

(g) performing reverse transcription extension using the poly T hybridization region as a primer, whereby a DNA strand is synthesized containing a barcode corresponding to a captured protein and a mRNA; and (h) preparing and sequencing a single composite sequencing library.

66. The method according to paragraph 65, wherein proteins are functionalized with biotin.

67. The method according to paragraph 66, wherein isolating oligo-aptamer protein complexes from oligo-aptamer molecules comprises streptavidin bead purification.

68. The method according to paragraph 65, wherein isolating oligo-aptamer protein complexes from oligo-aptamer molecules comprises conjugation of proteins to functionalized beads.

69. A method of identifying proteins and mRNAs expressed in single cells comprising:

(a) segregating single cells with a single solid support according to paragraph 18 by a method comprising merging one uniquely barcoded bead with a single-cell in an emulsion droplet, microfluidic drop, or microwell or a method comprising adding a single cell to a microwell comprising a barcoded surface, wherein the cells are lysed in a buffer that preserves aptamer-target recognition;

(b) incubating the lysed cells thereby capturing expressed aptamer target proteins and mRNAs on each bead or surface;

(c) wherein beads are used, breaking droplets or isolating beads from microwells and pooling the beads in solution;

(d) washing the beads or surfaces, wherein unbound proteins are removed;

(e) cleaving the linkers;

(f) isolating oligo-aptamer protein complexes from oligo-aptamer molecules;

(g) performing reverse transcription extension using the poly T hybridization region as a primer, whereby a DNA strand is synthesized containing a barcode corresponding to a captured protein and a mRNA; and (h) preparing and sequencing a single composite sequencing library.

70. The method according to paragraph 69, wherein the method further comprises covalently linking the aptamers to captured proteins after washing the beads or surfaces.

71. The method according to paragraph 69 or 70, wherein the method further comprises functionalizing proteins after washing the beads or surfaces or after covalently linking the aptamers to captured proteins.

72. The method according to paragraph 71, wherein said linkers are cleaved enzymatically, chemically or by UV treatment and said functionalizing proteins is performed before said cleavage.

73. The method according to paragraph 71, wherein said linkers are cleaved chemically or by UV treatment and said functionalizing proteins is performed after said cleavage.

74. The method according to any of paragraphs 71 to 73, wherein proteins are functionalized with biotin.

75. The method according to paragraph 74, wherein isolating oligo-aptamer protein complexes from oligo-aptamer molecules comprises streptavidin bead purification.

76. The method according to paragraph 69 or 70, wherein isolating oligo-aptamer protein complexes from oligo-aptamer molecules comprises conjugation of proteins to functionalized beads.

77. The method according to any of paragraphs 28 to 76, wherein the incubation is performed at 4 to 37° C.

78. A method of preparing oligonucleotide-adorned solid supports for identifying proteins expressed in single cells comprising:
(a) preparing solid supports linked to a plurality of oligonucleotides, each oligonucleotide comprising a linker directly attached to a solid support, a sequencing priming site, a cell barcode, and a hybridization sequence, optionally, a UMI; and
(b) adding to said solid supports a plurality of aptamer oligonucleotides, each aptamer oligonucleotide comprising a sequence complementary to the hybridization sequence, a target barcode specific for an aptamer, and an aptamer; and
(c) extending the oligonucleotides linked to the solid supports,
wherein the aptamer oligonucleotides comprising individual aptamers are pooled before adding to said solid supports, such that a desired ratio of individual aptamers is obtained on said solid supports.

79. The method according to paragraph 78, further comprising a spacer between the aptamer and the oligonucleotide strand, wherein the spacer functions as a blocking agent against DNA polymerase extension.

80. A method of preparing oligonucleotide-adorned solid supports for identifying proteins expressed in single cells comprising:
(a) preparing solid supports linked to a plurality of oligonucleotides, each oligonucleotide comprising a linker directly attached to a solid support, a sequencing priming site, a cell barcode, and a ligation sequence, optionally, a UMI; and
(b) adding to said solid supports for ligation, a plurality of aptamer oligonucleotides, each aptamer oligonucleotide comprising a hybridization sequence specific for the ligation sequence, a target barcode specific for an aptamer, and the aptamer; and
(c) ligating the oligonucleotides attached to the solid supports to the aptamer oligonucleotides,
wherein the aptamer oligonucleotides comprising individual aptamers are pooled before adding to said solid supports for ligation, such that a desired ratio of individual aptamers is obtained on said solid support.

81. The method according to any of paragraphs 78 to 80, wherein the cell barcode is prepared by at least two cycles of split and pool synthesis on the solid support.

82. The method according to any of paragraphs 78 to 81, wherein said oligonucleotides further comprise a reverse priming site after the target barcode sequence, whereby by the cell and target barcodes may be amplified by PCR.

83. The method according to any of paragraphs 78 to 82, wherein the solid support is a bead.

84. The method according to paragraph 83, wherein the bead is a magnetic bead.

85. The method according to paragraph 83, wherein the bead is a deformable bead.

86. The method according to paragraph 83, wherein the bead is a hydrogel bead.

87. The method according to any of paragraphs 78 to 82, wherein the solid support is a surface of a microwell.

88. The method according to paragraph 87, wherein the surface comprises a hydrogel surface.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed:

1. A plurality of oligonucleotide-adorned solid supports for the identification of a plurality of proteins expressed in single cells, wherein each solid support comprises a plurality of double stranded oligonucleotides, wherein only one strand of each double stranded oligonucleotide is attached to its solid support through a cleavable linker, wherein each of said double stranded oligonucleotides comprises:
(a) a sequence that serves as a sequencing priming site and is identical in each double stranded oligonucleotide from the plurality of solid supports;
(b) a cell barcode sequence, wherein the cell barcode sequence is the same across all double stranded oligonucleotides on the same solid support, but differs from the cell barcode sequence of the double stranded oligonucleotides on any other solid support from the plurality of solid supports;
(c) a target barcode sequence, wherein the target barcode sequence is specific to an individual aptamer;
(d) an aptamer conjugated to the unattached strand of the double stranded oligonucleotide, wherein the aptamer is specific to the target barcode sequence and configured for binding to a target protein; and
(e) a spacer between the aptamer and the oligonucleotide strand conjugated to said aptamer, wherein the spacer functions as a blocking agent against DNA polymerase extension,
wherein each solid supports binds to the same plurality of target proteins, and wherein each solid supports comprises more than one copy of oligonucleotides specific for each of the plurality of target proteins.

2. The plurality of oligonucleotide-adorned solid supports according to claim 1, wherein the copy number of double stranded oligonucleotides specific for different target proteins is varied on each of said solid supports and the variation in copy number is the same for each solid support; and/or
wherein each double stranded oligonucleotide further comprises a Unique Molecular Identifier (UMI) which differs for each double stranded oligonucleotide on a solid support; and/or
wherein said spacer comprises a C3 spacer; and/or
wherein each barcode ranges from 4 to 100 nucleotides in length; and/or
wherein the linker is chemically-cleavable, enzymatically cleavable, or photocleavable; and/or
wherein said double stranded oligonucleotides further comprise a reverse priming site after the target barcode sequence, whereby the cell and target barcodes may be amplified by PCR; and/or
wherein the solid supports are beads; or
wherein the solid supports are surfaces of microwells.

3. The plurality of oligonucleotide-adorned solid supports according to claim 1, wherein said double stranded oligonucleotides further comprise a 6 to 12 nucleotide universal hybridization sequence on the strand not conjugated to the aptamer, wherein said universal hybridization sequence is complementary to a hybridization sequence linked to a set of second oligonucleotide linked affinity reagents comprising an aptamer, antibody or antibody fragment.

4. The plurality of oligonucleotide-adorned solid supports according to claim 1, wherein said double stranded oligonucleotides further comprise a poly T sequence on the strand not conjugated to the aptamer, whereby the double stranded oligonucleotides are configured to capture polyadenylated mRNA.

5. The plurality of oligonucleotide-adorned solid supports according to claim 1, further comprising a plurality of second oligonucleotides on said solid supports, said second oligonucleotides comprising:
  (a) a second linker directly attached to the solid support, wherein the second oligonucleotide linker is chemically-cleavable, enzymatically cleavable, or photo-cleavable, wherein the second linker is different from the double stranded oligonucleotide linker, and wherein the second linker is capable of being cleaved without cleaving the double stranded oligonucleotide linker and wherein the double stranded oligonucleotide linker is capable of being cleaved without cleaving the second linker whereby each linker is capable of cleavage at different times;
  (b) a sequence in the second oligonucleotides that serves as a sequencing priming site and is identical in each second oligonucleotide from the plurality of solid supports;
  (c) the cell barcode sequence of the double stranded oligonucleotide on the same solid support;
  (d) a Unique Molecular Identifier (UMI) which differs for each second oligonucleotide on a solid support; and
  (e) an oligo dT sequence, whereby the solid support is configured to bind proteins and mRNAs.

6. The plurality of oligonucleotide-adorned solid supports according to claim 5, wherein the copy numbers of double stranded oligonucleotides specific for different target proteins and second oligonucleotides on said solid support are varied, such that the second oligonucleotides comprise 1-5% of oligonucleotides on said solid support and the double stranded oligonucleotides specific for different target proteins comprise 95-99% of oligonucleotides on said solid support.

7. A method of identifying proteins expressed in single cells comprising:
  (a) segregating single cells with single solid supports from the plurality of oligonucleotide-adorned solid supports according to claim 1 in emulsion droplets, microfluidic drops, or microwells;
  (b) lysing the cells and cleaving the linkers in a buffer that preserves aptamer-target recognition;
  (c) incubating the lysed cells and double stranded oligonucleotides, thereby capturing expressed aptamer target proteins on the cleaved double stranded oligonucleotides;
  (d) pooling the samples obtained by incubating the lysed cells and double stranded oligonucleotides;
  (e) optionally, functionalizing proteins;
  (f) isolating complexes of proteins bound to cognate aptamer-oligonucleotide conjugates from unbound aptamer-oligonucleotide conjugates; and
  (g) determining nucleotide sequences of cognate aptamer-oligonucleotide conjugates isolated in (f), whereby the cell barcodes record the cell-of-origin of each oligonucleotide sequence and target barcodes record expressed proteins from the same cell.

8. A method of identifying proteins expressed in single cells comprising:
  (a) segregating single cells with single solid supports from the plurality of oligonucleotide-adorned solid supports according to claim 1 in emulsion droplets, microfluidic drops, or microwells, wherein the cells are lysed in a buffer that preserves aptamer-target recognition;
  (b) incubating the lysed cells with the solid supports, thereby capturing expressed aptamer target proteins on each solid support;
  (c) washing the solid supports, wherein unbound proteins are removed;
  (d) cleaving the linkers;
  (e) isolating complexes of proteins bound to cognate aptamer-oligonucleotide conjugates from unbound aptamer-oligonucleotide conjugates; and
  (f) determining nucleotide sequences of cognate aptamer-oligonucleotide conjugates isolated in (e), whereby the cell barcodes record the cell-of-origin of each oligonucleotide sequence and target barcodes record expressed proteins from the same cell.

9. A method of identifying proteins and mRNAs expressed in single cells comprising:
  (a) segregating single cells with single solid supports from the plurality of oligonucleotide-adorned solid supports according to claim 5, wherein the cells are lysed in a buffer that preserves aptamer-target recognition;
  (b) incubating the lysed cells thereby capturing expressed aptamer target proteins on the double stranded oligonucleotides and mRNAs on the first and second oligonucleotides;
  (c) separating the double stranded oligonucleotides from the second oligonucleotides;
  (d) performing a reverse transcription reaction on the second oligonucleotides, whereby cDNA is obtained;
  (e) isolating complexes of proteins bound to cognate aptamer-oligonucleotide conjugates from unbound aptamer-oligonucleotide conjugates from the double stranded oligonucleotides; and
  (f) determining nucleotide sequences of cognate aptamer-oligonucleotide conjugates isolated in (e) and determining nucleotide sequences of cDNAs obtained in (d), wherein the second oligonucleotides are cleaved from the solid support before step (c), and wherein the double stranded oligonucleotides are cleaved after step (c) and before step (e).

10. The method according to claim 9, wherein segregating comprises merging ono segregating the solid supports with the single-cells in emulsion droplets, microfluidic drops, or microwells,
  optionally wherein after step (b) the solid supports are pooled in solution,
  optionally wherein step (c) comprises separating supernatants comprising cleaved second oligonucleotides,
  optionally wherein the solid supports are washed before cleavage of the second and/or double stranded oligonucleotides.

11. The method according to claim 10, wherein the method further comprises covalently linking the aptamers to captured proteins after washing the solid supports; and/or
  wherein the method further comprises functionalizing proteins after washing the solid supports or after covalently linking the aptamers to captured proteins, optionally wherein said double stranded oligonucleotide linkers or second linkers are cleaved enzymatically, chemically or by UV treatment and said functionalizing proteins is performed before said cleavage or optionally wherein said double stranded oligonucleotide linkers or second linkers are cleaved chemically or by UV treatment and said functionalizing proteins is performed after said cleavage.

12. The method according to claim 11, wherein proteins are functionalized with biotin and isolating complexes of proteins bound to cognate aptamer-oligonucleotide conjugates from unbound aptamer-oligonucleotide conjugates comprises streptavidin bead purification; or wherein isolating complexes of proteins bound to cognate aptamer-oligonucleotide conjugates from unbound aptamer-oligonucleotide conjugates comprises conjugation of proteins to functionalized beads.

13. A method of identifying proteins and mRNAs expressed in single cells comprising:
  (a) segregating single cells with single solid supports from the plurality of oligonucleotide-adorned solid supports according to claim 5 in emulsion droplets, microfluidic drops, or microwells, wherein the cells are lysed in a buffer that preserves aptamer-target recognition;
  (b) incubating the lysed cells thereby capturing expressed aptamer target proteins on the double stranded oligonucleotides and mRNAs on the second oligonucleotides on the solid supports;
  (c) washing the solid supports, wherein unbound proteins are removed;
  (d) cleaving the second oligonucleotide linkers;
  (e) separating the supernatant comprising second oligonucleotides from the solid supports;
  (f) performing a reverse transcription reaction on the supernatant, whereby the mRNA is converted to first strand cDNA;
  (g) cleaving the double stranded oligonucleotide linkers;
  (h) isolating complexes of proteins bound to cognate aptamer-oligonucleotide conjugates from unbound aptamer-oligonucleotide conjugates; and
  (i) determining nucleotide sequences of cognate aptamer-oligonucleotide conjugates isolated in (h) and determining nucleotide sequences of cDNAs obtained in (f).

14. The method according to claim 13, wherein the method further comprises covalently linking the aptamers to captured proteins after washing the solid supports; and/or wherein the method further comprises functionalizing proteins after washing the solid supports or after covalently linking the aptamers to captured proteins, optionally wherein said double stranded oligonucleotide linkers or second linkers are cleaved enzymatically, chemically or by UV treatment and said functionalizing proteins is performed before said cleavage or optionally wherein said double stranded oligonucleotide linkers or second linkers are cleaved chemically or by UV treatment and said functionalizing proteins is performed after said cleavage.

15. The method according to claim 14, wherein proteins are functionalized with biotin and isolating complexes of proteins bound to cognate aptamer-oligonucleotide conjugates from unbound aptamer-oligonucleotide conjugates comprises streptavidin bead purification; or wherein isolating complexes of proteins bound to cognate aptamer-oligonucleotide conjugates from unbound aptamer-oligonucleotide conjugates comprises conjugation of proteins to functionalized beads.

16. A method of identifying proteins and mRNAs expressed in single cells comprising:
  (a) segregating single cells with single solid supports from the plurality of oligonucleotide-adorned solid supports according to claim 5 in emulsion droplets, microfluidic drops, or microwells;
  (b) lysing the cells and cleaving the double stranded oligonucleotide linkers and second linkers in a buffer that preserves aptamer-target recognition;
  (c) incubating the lysed cells thereby capturing expressed aptamer target proteins on the cleaved double stranded oligonucleotides and mRNAs on the cleaved second oligonucleotides;
  (d) pooling the samples obtained by incubating the lysed cells;
  (e) optionally, functionalizing proteins;
  (f) isolating complexes of proteins bound to cognate aptamer-oligonucleotide conjugates from unbound aptamer-oligonucleotide conjugates oligo;
  (g) performing a reverse transcription reaction, whereby the mRNA is converted to first strand cDNA; and
  (h) determining nucleotide sequences of cognate aptamer-oligonucleotide conjugates isolated in (f) and determining nucleotide sequences of cDNAs obtained in (g).

17. A method of identifying proteins that are in proximity in single cells or identifying post-translationally modified proteins expressed in single cells comprising:
  (a) segregating single cells with single solid supports from the plurality of oligonucleotide-adorned solid supports according to claim 3 in emulsion droplets, microfluidic drops, or microwells, wherein the cells are lysed in a buffer that preserves aptamer-target recognition;
  (b) incubating the lysed cells thereby capturing complexes of proteins bound to cognate aptamer-oligonucleotide conjugates on the solid supports;
  (c) washing the solid supports, wherein unbound proteins are removed;
  (d) incubating the captured complexes of proteins bound to cognate aptamer-oligonucleotide conjugates with a set of second oligonucleotide linked affinity reagents comprising i) an aptamer, antibody or antibody fragment, ii) a sequencing primer sequence, iii) a target barcode and iv) a 6 to 12 nucleotide hybridization sequence, wherein when a second affinity reagent binds to a protein that is interacting with a captured protein or to a post: translational modification on a captured protein the hybridization sequence binds to the universal hybridization sequence;
  (e) washing the solid supports, wherein unbound second affinity reagents are removed;
  (f) performing DNA polymerase extension of the universal hybridization sequence into the hybridized second oligonucleotide sequence linked to an affinity reagent, whereby a DNA strand is synthesized comprising the barcodes corresponding to both proteins or to both target protein and target post translational modification; and
  (g) determining nucleotide sequences of DNA strands synthesized in (f), whereby the cell barcodes record the cell-of-origin of each oligonucleotide sequence and target barcodes record the proteins in proximity or the target protein and target post: translational modification.

18. A method of identifying proteins and mRNAs expressed in single cells comprising:
  (a) segregating single cells with single solid supports from the plurality of oligonucleotide-adorned solid supports according to claim 4 in emulsion droplets, microfluidic drops, or microwells;

(b) lysing the cells and cleaving the linkers in a buffer that preserves aptamer-target recognition;
(c) incubating the lysed cells and double stranded oligonucleotides thereby capturing expressed aptamer target proteins and mRNAs on the cleaved double stranded oligonucleotides;
(d) optionally, functionalizing proteins;
(e) isolating complexes of proteins bound to cognate aptamer-oligonucleotide conjugates from unbound aptamer-oligonucleotide conjugates;
(f) performing reverse transcription extension using the poly T hybridization region as a primer, whereby a DNA strand is synthesized containing a barcode corresponding to a captured protein and a mRNA; and
(g) determining nucleotide sequences of DNA strands synthesized in (f).

19. A method of identifying proteins and mRNAs expressed in single cells comprising:
(a) segregating single cells with single solid supports from the plurality of oligonucleotide-adorned solid supports according to claim 4 in emulsion droplets, microfluidic drops, or microwells, wherein the cells are lysed in a buffer that preserves aptamer-target recognition;
(b) incubating the lysed cells thereby capturing expressed aptamer target proteins and mRNAs on each solid support;
(c) washing the solid supports, wherein unbound proteins are removed;
(d) cleaving the linkers;
(e) isolating complexes of proteins bound to cognate aptamer-oligonucleotide conjugates from unbound aptamer-oligonucleotide conjugates;
(f) performing reverse transcription extension using the poly T hybridization region as a primer, whereby a DNA strand is synthesized containing a barcode corresponding to a captured protein and a mRNA; and
(g) determining nucleotide sequences of DNA strands synthesized in (f).

20. The method according to claim 19, wherein the method further comprises covalently linking the aptamers to captured proteins after washing the solid supports; and/or
wherein the method further comprises functionalizing proteins after washing the solid supports or after covalently linking the aptamers to captured proteins; or
wherein isolating complexes of proteins bound to cognate aptamer-oligonucleotide conjugates from unbound aptamer-oligonucleotide conjugates comprises conjugation of proteins to functionalized beads.

21. The method according to claim 20, wherein said linkers are cleaved enzymatically, chemically or by UV treatment and said functionalizing proteins is performed before said cleavage; or wherein said linkers are cleaved chemically or by UV treatment and said functionalizing proteins is performed after said cleavage.

22. The plurality of oligonucleotide-adorned solid supports according to claim 1, wherein said aptamers further comprise a photoreactive group configured to covalently link the aptamers to captured proteins upon illumination.

23. The plurality of oligonucleotide-adorned solid supports according to claim 2, wherein the UMI comprises 6 to 20 nucleotides in length.

24. The plurality of oligonucleotide-adorned solid supports according to claim 2, wherein the beads are a hydrogel beads, deformable beads or magnetic beads.

25. The plurality of oligonucleotide-adorned solid supports according to claim 2, wherein the surfaces comprises hydrogel surfaces.

26. The plurality of oligonucleotide-adorned solid supports according to claim 5, wherein the UMI comprises 6 to 20 nucleotides in length.

27. The method according to claim 7, wherein the incubation is performed at 4 to 37° C.; and/or
wherein the proteins are functionalized with biotin; and/or
wherein isolating complexes of proteins bound to cognate aptamer-oligonucleotide conjugates from unbound aptamer-oligonucleotide conjugates comprises streptavidin bead purification or conjugation of proteins to functionalized beads.

28. The method according to claim 8, wherein the incubation is performed at 4 to 37° C.; and/or
wherein the method further comprises covalently linking the aptamers to captured proteins after washing the solid supports and/or functionalizing proteins after washing the solid supports or after covalently linking the aptamers to captured proteins; and/or
wherein said linkers are cleaved enzymatically, chemically or by UV treatment and said functionalizing proteins is performed before said cleavage or wherein said linkers are cleaved chemically or by UV treatment and proteins are functionalized after said cleavage; and/or
wherein proteins are functionalized with biotin and wherein isolating complexes of proteins bound to cognate aptamer-oligonucleotide conjugates from unbound aptamer-oligonucleotide conjugates comprises streptavidin bead purification or wherein isolating complexes of proteins bound to cognate aptamer-oligonucleotide conjugates from unbound aptamer-oligonucleotide conjugates comprises conjugation of proteins to functionalized beads.

29. The method according to claim 9, wherein the incubation is performed at 4 to 37° C.

30. The method according to claim 13, wherein the incubation is performed at 4 to 37° C.

31. The method according to claim 16, wherein the incubation is performed at 4 to 37° C.; and/or
wherein proteins are functionalized with biotin and isolating complexes of proteins bound to cognate aptamer-oligonucleotide conjugates from unbound aptamer-oligonucleotide conjugates comprises streptavidin bead purification or preferably wherein isolating complexes of proteins bound to cognate aptamer-oligonucleotide conjugates from unbound aptamer-oligonucleotide conjugates comprises conjugation of proteins to functionalized beads.

32. The method according to claim 17, wherein the incubation is performed at 4 to 37° C.

33. The method according to claim 18, wherein the incubation is performed at 4 to 37° C.; and/or
wherein proteins are functionalized with biotin and isolating complexes of proteins bound to cognate aptamer-oligonucleotide conjugates from unbound aptamer-oligonucleotide conjugates comprises streptavidin bead purification or wherein isolating complexes of proteins bound to cognate aptamer-oligonucleotide conjugates from unbound aptamer-oligonucleotide conjugates comprises conjugation of proteins to functionalized beads.

34. The method according to claim 19, wherein the incubation is performed at 4 to 37° C.

35. The method according to claim 20, wherein proteins are functionalized with biotin and isolating complexes of proteins bound to cognate aptamer-oligonucleotide conjugates from unbound aptamer-oligonucleotide conjugates comprises streptavidin bead purification.

* * * * *

UNITED STATES PATENT AND TRADEMARK OFFICE
CERTIFICATE OF CORRECTION

| | | |
|---|---|---|
| PATENT NO. | : 11,072,816 B2 | Page 1 of 3 |
| APPLICATION NO. | : 15/970791 | |
| DATED | : July 27, 2021 | |
| INVENTOR(S) | : Jellert Gaublomme et al. | |

It is certified that error appears in the above-identified patent and that said Letters Patent is hereby corrected as shown below:

On the Title Page

On the page 2, in Column 2, item (56) under "Other Publications", Line 5, delete "illumina I Bio-Rad," and insert -- illumina|Bio-Rad, --.

On the page 3, in Column 2, item (56) under "Other Publications", Lines 38-39, delete "illumina I Bio-Rad," and insert -- illumina|Bio-Rad, --.

On the page 3, in Column 2, item (56) under "Other Publications", Line 41, delete "illumina I Bio-Rad," and insert -- illumina|Bio-Rad, --.

In the Specification

In Column 12, Lines 50-63, delete "FIG. 1C shows the oligonucleotide comprising a NXT hybridization sequence, cellular barcode 1, and hybridization 1 sequence is hybridized to the common primer and is extended. FIG. 1D, FIG. 1E and FIG. 1F shows the oligonucleotide with a complementary hybridization 1 sequence, cellular barcode 2, and hybridization 2 sequence is hybridized to the prior primer and is extended in both directions. FIG. 1G and FIG. 1H show a custom synthesized aptamer oligonucleotide with a complementary hybridization 2 sequence, protein barcode, UMI, sequencing primer NXT2, spacer, and the aptamer oligonucleotide is hybridized to the prior primer and is extended in both directions. Extension is stopped by the spacer." and insert the same on Column 12, Line 49 as the continuation of the same paragraph.

In Column 13, Line 47, delete "2nd" and insert -- $2^{nd}$ --.

In Column 13, Line 49, delete "4th" and insert -- $4^{th}$ --.

In Column 13, Line 54, delete "Laboratory Manual" and insert -- Laboratory-Manual --.

In Column 13, Line 55, delete "Laboratory Manual, 2nd" and insert -- Laboratory-Manual, $2^{nd}$ --.

Signed and Sealed this
Fifth Day of April, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,072,816 B2

In Column 14, Line 2, delete "2nd" and insert -- $2^{nd}$ --.

In Column 14, Line 18, delete "+1-10%" and insert -- +/-10% --.

In Column 16, Line 28, delete "2'-F)," and insert -- (2'-F), --.

In Column 16, Line 40, delete "example;" and insert -- example, --.

In Column 16, Line 46, delete "Res," and insert -- Res. --.

In Column 25, Line 22, delete "U.S.A" and insert -- U.S.A. --.

In Column 30, Lines 7-8, delete "www.10×genomics.com/technology)," and insert -- www.10xgenomics.com/technology), --.

In Column 35, Line 20, delete "10.1016/j.ce11.2014.09.014(2014);" and insert -- 10.1016/j.cell.2014.09.014(2014); --.

In Column 39, Line 62, delete "Fokl" and insert -- FokI --.

In Column 39, Line 67, delete "Fokl" and insert -- FokI --.

In Column 42, Line 4, delete "1)/iSpPC/Photocleavable" and insert -- 1) /iSpPC/ Photocleavable --.

In Column 42, Line 6, delete "2)/ideoxyU/Enzymatically" and insert -- 2) /ideoxyU/ Enzymatically --.

In Column 45, Line 39, delete "co-encapuslation" and insert -- co-encapsulation --.

In the Claims

In Column 58, Line 39, in Claim 1, delete "supports" and insert -- support --.

In Column 58, Line 40, in Claim 1, delete "supports" and insert -- support --.

In Column 59, Line 24, in Claim 5, delete "linker" and insert -- linker, --.

In Column 60, Line 30, in Claim 9, after "on the" delete "first and".

In Column 60, Line 48, in Claim 10, after "comprises" delete "merging ono".

In Column 62, Line 17, in Claim 16, delete "conjugates oligo;" and insert -- conjugates; --.

In Column 62, Line 44, in Claim 17, delete "post: translational" and insert -- post-translational --.

In Column 62, Line 60, in Claim 17, delete "post: translational" and insert -- post-translational --.

CERTIFICATE OF CORRECTION (continued)
U.S. Pat. No. 11,072,816 B2

In Column 63, Line 63, in Claim 24, after "are" delete "a".

In Column 63, Line 66, in Claim 25, delete "comprises" and insert -- comprise --.

In Column 64, Line 45, in Claim 31, after "or" delete "prcfcrably".